(12) United States Patent
Greenwood et al.

(10) Patent No.: US 7,600,703 B2
(45) Date of Patent: Oct. 13, 2009

(54) PARTICLE-SIZE REDUCTION APPARATUS AND USE THEREOF

(75) Inventors: Alan K. Greenwood, Stevenage (GB); Parveen Bhatarah, Stevenage (GB); Gary Hembra, Stevenage (GB); Derek McHattie, Stevenage (GB)

(73) Assignee: Resolution Chemicals Limited, Hertfordshire (GB)

( * ) Notice: Subject to any disclaimer, the term of this patent is extended or adjusted under 35 U.S.C. 154(b) by 106 days.

(21) Appl. No.: 10/568,726

(22) PCT Filed: Aug. 19, 2004

(86) PCT No.: PCT/GB2004/003574

§ 371 (c)(1),
(2), (4) Date: Aug. 21, 2006

(87) PCT Pub. No.: WO2005/018687

PCT Pub. Date: Mar. 3, 2005

(65) Prior Publication Data
US 2006/0280643 A1  Dec. 14, 2006

(30) Foreign Application Priority Data
Aug. 19, 2003 (GB) .................................. 0319500.5

(51) Int. Cl.
*B02C 19/06* (2006.01)
(52) U.S. Cl. ............................................. 241/5; 241/39
(58) Field of Classification Search .................. 241/5, 241/39, 40
See application file for complete search history.

(56) References Cited

U.S. PATENT DOCUMENTS

| 3,667,688 | A |   | 6/1972 | Iannicelli |
|---|---|---|---|---|
| 4,895,876 | A | * | 1/1990 | Schweighardt et al. ...... 514/747 |
| 5,810,267 | A |   | 9/1998 | Karasawa |
| 6,187,765 | B1 | * | 2/2001 | Harris et al. ................ 514/172 |
| 6,464,958 | B1 |   | 10/2002 | Bernini et al. |
| 2002/0071870 | A1 |   | 6/2002 | Sharma |

FOREIGN PATENT DOCUMENTS

| EP | 0601724 | 6/1994 |
|---|---|---|
| GB | 285258 | 2/1928 |
| GB | 1049685 | 11/1966 |
| GB | 2275876 | 9/1994 |
| JP | 11042428 | 2/1999 |
| RU | 2080165 | 5/1997 |
| WO | WO-92/09368 | 6/1992 |
| WO | WO-94/08719 | 4/1994 |
| WO | WO-99/07466 | 2/1999 |
| WO | WO-99/25359 | 5/1999 |
| WO | WO-00/25745 | 5/2000 |
| WO | WO-03/070285 | 8/2003 |
| WO | WO-2004/087204 | 10/2004 |

* cited by examiner

*Primary Examiner*—Mark Rosenbaum
(74) *Attorney, Agent, or Firm*—Marshall, Gerstein & Borun LLP

(57) ABSTRACT

A sterilisable particle-size reduction apparatus, component parts thereof and a method of sterilizing and validating sterility thereof are provided. Also provided is use thereof to prepare sterile suspensions of drugs.

11 Claims, 13 Drawing Sheets

PARTICLE-SIZE REDUCTION APPARATUS AND USE THEREOF

This application claims priority of United Kingdom Patent Application Serial No. 0319500.5 filed Aug. 19, 2003, and PCT Patent Application Number PCT/GB2004/003574, filed Aug. 8, 2004.

This invention relates to a particle-size reduction apparatus, component parts therefor and use thereof to prepare suspensions of drugs, in particular for administration via nebulizers.

Previously it was acceptable for drugs intended for use in nebulizers to be prepared under "clean" conditions. Recently, however, such formulations have caused problems in the US due to contamination, and the US FDA has implemented a requirement for all nebulizer solutions to be sterile. In the light of the US FDA decision it is necessary to produce sterile suspension drugs in the US.

The sterilisation of suspensions raises particular problems. The standard means of sterilisation—that is, the raising of the temperature of the formulation to 121° C. for 15 minutes—frequently destroys one or more of the components of the formulation, so only chemically thermostable products can be sterilised by this method. The desired biological activity of the formulation commonly requires that the mass median diameter of particles of the drug lies within a narrow range (average diameter typically less than 5 micrometres). End sterilisation may alter particle size. In addition this treatment results in the clumping or agglomeration of the drug particles in the suspension such that the efficacy of the resulting product is impaired or abolished.

Known alternative methods for the sterilisation of pharmaceuticals are inappropriate for sterilising suspension formulations of drugs. Solutions of pharmaceuticals may be sterilised by passage though a filter having a pore size of not more than 0.2 μm. However this cannot be used in the case of suspensions as the required particle size in these formulations (typically 2-5 μm) is significantly greater than this filter pore size. Similarly, pharmaceuticals may generally be sterilised by gamma-irradiation, but Budesonide, for example, is destroyed by such treatment (see for example, WO 00/25745). Cold sterilisation using ethylene oxide and carbon dioxide is also known, but stability of Budesonide under these sterilisation conditions has yet to be demonstrated. No further methods for the sterilisation of pharmaceuticals are currently acceptable to regulatory agencies.

Drugs typically provided as nebule suspensions are the steroids Fluticasone and Budesonide, used to treat asthma and chronic obstructive pulmonary disorder. These drugs are very insoluble in water and are sold as non-sterile powders.

A method of sterilising dry, powdered Budesonide is known from WO 99/25359. This method of sterilisation is problematic as it requires Budesonide powder to be sterilised and then mixed with the other components of the formulation under sterile conditions. The drug formulation is subsequently prepared under sterile conditions.

International Application No. PCT/GB03/00702 (incorporated herein by reference) describes a solvent based sterilisation method for sterilising pharmaceuticals, in particular suspensions of drugs for use in nebulizers. A sterile composition of a pharmaceutical compound is prepared by combining solvent with a non-sterile pharmaceutical compound to form a solution and then filtering the solution, to yield a sterile pharmaceutical compound. All or part of the solvent is optionally removed to form a suspension, and under sterile conditions the compound is combined with a pharmaceutically acceptable carrier.

In order to be effective in the lungs, the particle size of an active ingredient in a suspension must be within a certain size range-typically the mass median diameter of the particles in the suspension is less than 10 μm. The sterile suspension may, therefore, be passed through a particle-size reduction apparatus, such as a homogenizer, Microfluidizer(®) or similar device to reduce the average mass median diameter of the particles.

A suitable device, referred to as a Microfluidizer(®), is available from Microfluidics, Inc. (MFIC), described in WO 99/07466 (incorporated herein by reference). Examples of Microfluidizer(®) apparatus suitable for production scale particle-size reduction of a pharmaceutical suspension include the M-610 and M-210EH series machines but these devices can not be sterilised.

Particle-size reduction apparatus such as the Microfluidizer(®) apparatus typically operate under high pressures and comprise a plunger and a seal to separate the high pressure end of the apparatus from the low pressure end.

It is extremely important that the plunger seal maintains its integrity throughout the particle-size reduction process because if the seal were to fail, the sterility of the process could be compromised. The seal is therefore a high maintenance component that needs to be regularly removed for inspection and/or replaced.

Methods and apparatus are known in the art for removing a seal from and inserting a seal into a Microfluidizer(®). A seal is conventionally removed from a bore, such as the bore of a particle-size reducing apparatus, according to the following method. The end of the apparatus barrel is plugged with an appropriate plug and placed in a sink on a sponge. The barrel is then filled with water to within 1 cm of the seal. A seal removal rod is inserted into the barrel and a paper towel is draped around the seal removal rod to prevent water from splashing. The plunger removal rod is then given a sharp blow with a mallet, causing the water to push the seal components out of the bore for easy removal.

To install a new seal into the bore, the seal is inserted into a seal holder, such as the seal holder supplied by MFIC. Care must be taken at this stage not to damage the sealing lips. The large diameter of the seal locator is then placed against the lips of the cup seal and used to push the seal until it bottoms against the seal holder. The seal holder is then inverted and positioned over the apparatus barrel seal cavity. The smaller diameter of the seal locator is now placed into the seal holder and, using a mallet, a sharp blow is administered to position the seal in the seal cavity. The remaining seal components are now placed into the seal cavity by hand, taking great care to ensure that they are orientated correctly and in the right order.

There are a number of problems associated with the above-described conventional methods. General disadvantages of these methods are that they are very messy and time-consuming to operate. A particular problem is the potential for human error when inserting the seal components—for example, inserting the components in the incorrect order or orientation. Incorrect or inaccurate placement of the seal in the barrel may damage the seal and possibly result in seal failure in use. Removal of a seal by the conventional method frequently damages the seal, preventing re-use and making it difficult to tell at which stage the damage occurred.

A further disadvantage of the conventional seal removal method is that this method cannot be used to validate the sterility of the particle-size reducing apparatus. The conventional method washes micro-organisms off the seal, thus compromising the validation, and is generally less clean.

It is an object of the invention to overcome or at least ameliorate the identified problems, and specifically to provide a sterilisable particle-size reduction apparatus, including adaptations to render existing apparatus, when adapted, sterilisable.

Objects of specific embodiments of the invention include sterilising a particle-size reduction apparatus and verifying the sterility of a particle-size reduction apparatus, and reducing the size of particles in a sterile suspension, without compromising sterility of the suspension.

Objects of further specific embodiments of the invention include providing alternative, preferably improved, apparatus for inserting a seal into a bore, a method of accurately positioning a seal into a bore, and an alternative apparatus and method for removing a seal from a bore. In particular, an object is to provide a seal retractor that can remove a seal from a bore so that the seal can be used to validate the sterility of the bore.

Accordingly, the present invention provides a sterilisable particle-size reduction apparatus, particular components therefor, methods of sterilising the apparatus and use of the apparatus to adjust the particle size distribution of a suspension under sterile conditions. The invention includes, in specific aspects, individual components for a particle-size reduction apparatus and specified modifications for existing such apparatus, which modifications or components result in an apparatus adapted to be sterilised.

The present invention provides a sterilisable particle-size reduction apparatus, comprising an interaction chamber, for reducing the particle-size of a suspension, and an intensifier, for introducing the suspension into the interaction chamber at high pressure.

The invention further provides a method of producing a comminuted suspension of particles, which comprises:

subjecting an initial suspension of particles to a comminution procedure carried out in a sterilised particle size reduction apparatus, said particle size reduction apparatus comprising an interaction chamber, for reducing the particle-size of the suspension, and an intensifier for introducing the suspension into the interaction chamber at high pressure, and recovering a suspension of particles of reduced size, characterised in that components of the particle size reduction apparatus are sterilisable and the method includes a sterilisation step in which at least surfaces of the apparatus contacting the suspension are sterilised.

The particle-size reduction apparatus may be any device which achieves reduction of the mass median diameter of particles in a suspension. In a particular embodiment, the apparatus is a Microfluidizer(®)—suitably model M-110, M-610, or M-210EH, adapted according to the invention to be sterilisable.

Particular adaptations are set out below, and described in more detail in a specific embodiment of the invention. In general, to be sterilisable, apparatus of the invention comprise at least one, preferably two or more of the following features:

(a) there is no conduit between the output and input of the intensifier other than via the interaction chamber;
(b) valves in conduits between the intensifier and the interaction chamber are diaphragm needle valves;
(c) non-return valves in the apparatus have metal-to-metal seats;
(d) the plunger seal in the intensifier is adapted to be sterilised;
(e) the bushing assembly in the intensifier allows access of sterilising steam or water to the plunger seal;
(f) the cam nut in the intensifier is adapted to be sterilised;
(g) a rupture disc is used as a pressure relief valve; and
(h) a seal is provided to prevent suspension from reaching the oil that drives the intensifier in the event of failure of the plunger seal.

By "sterilisable" it is meant that sterility sufficient to satisfy MCA and FDA regulations for pharmaceutical use is achieved. By way of example, at the present time, the MCA requires a 6 log reduction in suitably heat-resistant bacterial spores (e.g. *Geobacillus stearothermophilus*, ATCC No. 7953) to be demonstrated—that is, that the number of spores present after sterilisation is reduced by 6 log in comparison to the number of spores present before sterilisation. In one embodiment, to demonstrate sterilisation, a challenge of heat-resistant bacterial spores in excess of 1 million is administered and then sterilisation carried out. If total kill of spores is demonstrated then sterilisation has been demonstrated. The FDA may allow an extrapolation of sterility from a short time period. Hence, if a 3 log reduction is demonstrated in x minutes then the FDA may allow an extrapolation to a 6 log reduction in 2x minutes.

By "high pressure" it is meant pressures in excess of 5000 psi, preferably in excess of 10,000 psi, more preferably in excess of 20,000 psi and in a particular embodiment up to around 30,000 psi. In typical operation of the apparatus, oil at a pressure of up to 5,000 psi is used to drive a piston in the intensifier, resulting in a pressure in the plunger barrel of the intensifier of up to 30,000 psi. Hence, suspension exits the plunger barrel of the intensifier at this pressure and is directed to the interaction chamber or chambers, and on exiting the last interaction chamber generally has a pressure which has reduced to below about 100 psi. Operating using these pressures, the apparatus described in a specific embodiment processes approximately 1.2 liters of suspension per minute. A typical batch is 12 liters and is passed about 14 times through the apparatus, which takes approximately 140 minutes.

The intensifier suitably comprises an output and an input, and the interaction chamber comprises an input and an output, the output of the intensifier being connected to the input of the interaction chamber and the output of the interaction chamber being connected to the input of the intensifier, and there is no conduit between the output of the intensifier and the input of the intensifier other than via the interaction chamber. This means that all the suspension leaving the intensifier at high pressure must travel through the interaction chamber, in which particle-size reduction takes place, before exiting the apparatus. In particular this means that the sterilisable particle-size reduction apparatus of the present invention does not comprise a bypass line that would allow product (and sterilising steam or water) to bypass the interaction chamber, as the presence of such a line means that section of the apparatus cannot be sterilised.

The apparatus is routinely supplied with more than one (most often two) interaction chambers in series, with the first interaction chamber having internal conduits of the smallest size, preferably in the range from 10 µm, more preferably 30 µm to 150 µm, more preferably to 100 µm, and the second interaction chamber having internal conduits of larger size, preferably in the range from 200 µm, more preferably 300 µm to 600 µm, more preferably to 500 µm. The M-120EH machine is supplied with interaction chambers in which the first chamber has conduits with dimensions down to approximately 78 µm and the next chamber with dimensions down to approximately 400 µm, and this arrangement has been found acceptable for reduction, under sterile conditions, of the mass median diameter of a Budesonide suspension down to 2 µm-5 µm. It is an option, though, to reverse the order of the interaction chambers and we have found that best results are achieved, in reducing the particle size of a suspension of Budesonide, when the suspension exiting the intensifier passes first into a interaction chamber with larger conduit size and then into an interaction chamber with smaller conduit size.

The intensifier and interaction chambers are linked by conduits and the conduits are generally provided with a number of valves to control or direct flow of material. In one embodiment, the valves in the conduits between the intensifier and the interaction chamber are sterilisable diaphragm needle valves. Other valves in the apparatus are non-return valves, which prevent flow of suspension in the wrong direction—that is, the non-return valves ensure a flow of product in one direction from the intensifier to the interaction chamber. Preferably, the non-return valves in conduits between the intensifier and the interaction chamber have metal-to-metal seats. The provision of metal-to-metal seats enables effective sterilisation of the non-return valves in situ.

In particular apparatus, the intensifier comprises a bore and a reciprocating plunger and a seal between the plunger and the bore. The purpose of the seal is to separate the high pressure side of the intensifier from the low pressure side. The seal must therefore be able to withstand high pressures without extruding or otherwise failing. A preferred seal, used in apparatus of the invention, is adapted to be sterilisable, preferably incorporating a brace to prevent sides of the seal from collapsing, which brace is made of or comprises a resilient plastics material. The seal is described in more detail below.

In other particular apparatus, the intensifier comprises a reciprocating plunger and a bushing assembly to guide the plunger as it reciprocates within the plunger chamber or barrel. The bushing assembly preferably comprises a bushing holder and a bushing supported within the bushing holder. This bushing assembly preferably comprises a channel in or on the surface of the bushing assembly, to allow sterilising steam or water to pass through the bushing assembly whilst the plunger is in place. The channel in or on the surface of the bushing assembly may typically be a groove or a conduit, and may be located on the outer or inner surface of the bushing and/or on the bushing holder. The groove or conduit may be of any dimensions and there may be any number of grooves or conduits, enabling steam or water to pass through the bushing assembly whilst the plunger is in place. This bushing assembly means that sterilising steam or sterilising water has access through the bushing to components of the apparatus that would otherwise be difficult or impossible to sterilise, and this arrangement especially allows access of sterilising water or steam to the back of the plunger seal.

Referring to the apparatus in the figures, one end of the intensifier plunger is connected via a threaded cam nut to a connecting rod having a screw thread to receive the cam nut. The dimensions of the screw thread and the thread of the cam nut are such that as the nut is screwed onto the connecting rod (con rod), respective mating surfaces on the cam nut and the con rod mate simultaneously, which avoids nooks and crannies that may harbour microorganisms and thus renders this portion of the apparatus sterilisable. The plunger in use bears on the front end of the con rod and is held loosely in place by the cam nut. As the plunger is driven in one direction, the cam nut approaches and then hits and triggers an air switch, changing the direction of flow of oil from oil lines to the piston around the con rod and sending the plunger back in the reverse direction.

Optionally, a heat exchanger is provided to control the temperature of the suspension and preferably to maintain it at from 7° C. to 40° C. in use. If the suspension is a drug suspension, it is important to maintain the temperature within a certain range because some drugs are susceptible to heat degradation. By way of example, Budesonide may be degraded by long exposure to temperatures above 40° C., so during Budesonide processing the temperature is preferably maintained below 50° C., more preferably below 40° C. A further use of the heat exchanger is during sterilisation of the apparatus. Time is spent heating various components of the apparatus up to the sterilising temperature. Therefore, in a preferred method of sterilisation, the heat exchanger is used to heat the interaction chamber or chambers, and preferably also the piping immediately surrounding the chambers, to reduce the time required for the interaction chambers to reach the required temperature. In a further preferred embodiment, the apparatus comprises a first heat exchanger to maintain the temperature of the suspension in the interaction chamber and a second heat exchanger to maintain the temperature of the suspension in the intensifier, wherein the first and second heat exchangers are independently controlled.

The apparatus optionally comprises at least one pressure relief valve, so that if excessive pressure builds up on the low pressure side of the apparatus, that is to say downstream of the interaction chamber, this pressure can be relieved instead of leading to damage of the low pressure side. The valve is preferably a rupture disc. By rupture disc it is meant a valve that bursts if the pressure at the valve exceeds a certain value. Hence, the rupture disc acts as a safety mechanism, to alert an operator to the fact that a pressure exceeding the specified value has been reached at that point in the apparatus. This could typically occur if one of the non-return valves of the apparatus has failed or if there is a blockage in the return line. In one embodiment, the rupture disc will burst if the pressure at the disc exceeds 150 psi. In another embodiment, the rupture disc is positioned so as to prevent damage to the interaction chamber and associated pipework and valves should the plunger seal fail. During operation of the apparatus, once the apparatus has been sterilised it is used to reduce the particle size of a sterile suspension. If there were to be a failure, possibly a transient failure, leading to excess pressure on the low pressure side of the apparatus then rupture of the disc alerts the operator to the failure. That batch is then discarded, as the failure would indicate a risk of contamination, leading to production of a non-sterile suspension. Hence, an advantage of using this rupture disc is that a transient failure, which in the art would be accommodated by transient opening and closing of a standard relief valve, does not mask a failure of sterility in the apparatus and hence in the suspension being processed.

Particular apparatus further comprise a seal that prevents suspension from reaching the oil that drives the intensifier in the event of failure of the plunger seal. It is advantageous to prevent suspension from interfering with the hydraulic pump section of the apparatus if the plunger seal fails. This seal is typically capable of withstanding pressures of 150 psi at 200° C. while the plunger is moving. Preferably, this seal is a lip-type seal and is manufactured from PTFE. The seal may further comprise a metal coiled support inner spring to help avoid collapse, extrusion or distortion at high temperature.

In an example of using the apparatus, product is processed in several cycles. In each cycle, product is passed from a feed tank into the particle-size reduction apparatus. As the cycle progresses, product accumulates in a recycle tank. Once the feed tank is empty or nearly empty, a cycle is deemed to be finished, and the feed tank is then re-filled from the recycle tank, indicating that a further cycle is beginning. We have circulated a suspension of Budesonide in water and Tween approximately 14 times in order to achieve a desired particle size distribution of 2-3 μm. It is also possible to circulate the suspension with the apparatus operating at lower pressure, in which case a larger number of cycles would be needed to achieve the same particle size distribution.

The invention also provides individual components of the sterilisable particle-size reduction apparatus.

The invention further provides a bushing assembly, for use with a cylindrical plunger, comprising a bushing holder and a bushing, held in place by the bushing holder, wherein the bushing assembly comprises one or more conduits to allow passage of sterilising steam or water therethrough.

The invention also provides a bushing assembly for a plunger that reciprocates in a plunger barrel, comprising a bushing holder which attaches to a neck of the barrel and a bushing held in situ by the bushing holder and which guides the plunger into and out of the barrel, wherein the bushing and/or the bushing holder comprises one or more conduits to allow passage of sterilising steam or water through the bushing assembly.

During sterilisation of the apparatus, the conduits allow access of sterilising water or steam to parts of the apparatus which might otherwise be difficult or impossible to sterilize. In particular, sterilising water or steam can now have access to the plunger seal. During sterilisation, sterilising water or steam passes through the bushing assembly and sterilizes the back of the plunger seal. Usually, whilst sterilisation is taking place, the apparatus is run at a reduced rate, enabling sterilisation of all parts of the intensifier, both the high pressure side and the low pressure side, the high pressure side being sterilised by steam introduced directly into the plunger barrel.

The plunger barrel may, for instance, be the plunger barrel of a particle-size reduction apparatus, such as a Microfluidizer(®).

By conduits it is meant grooves, channels or the like through which the steam or water may pass. The grooves or channels may be of any dimensions, so long as passage of the steam or water therethrough is permitted.

Said grooves may be located anywhere on the outer or inner surface of the bushing and may be aligned in any direction, so long as they permit passage of steam or water through the bushing assembly. In one embodiment, the bushing comprises one or more grooves located on its outer surface. Alternatively, or in addition, said bushing may comprise one or more grooves located on its inner surface. The grooves may be parallel to the longitudinal axis of the bushing or said grooves may be formed in a spiral around the longitudinal axis of the bushing.

It is an option for the bushing assembly to comprise a bushing which comprises one or more grooves and a bushing holder which comprises one or more grooves or one or more conduits to allow passage of steam or water therethrough.

Where both the bushing and the bushing holder comprise one or more grooves, it is preferred for said one or more grooves of said bushing and bushing holder to be in alignment as this enables unhindered passage of steam through the bushing apparatus. Alignment of said one or more grooves of the bushing and the bushing holder can be achieved using a bushing assembly wherein said bushing further comprises one or more projections that cooperate with one or more recesses in said bushing holder in order to align said one or more grooves of said bushing with those of the bushing holder. Alternatively said bushing holder has one or more projections that cooperate with one or more recesses in the bushing.

The invention also provides an annular high-pressure seal, for a plunger reciprocating within a barrel, comprising lower and upper body portions, said upper portion being in the form of a cup and having sides surrounding a recess, the sides being outwardly deformable so that respective outer and inner edges of the sides of the cup make, in use, sealing contact with respectively the barrel and the plunger, the seal further comprising a brace to prevent the sides from collapsing into the recess under low pressure and wherein the brace comprises a resilient plastics material.

By "high-pressure seal" it is meant a seal capable of withstanding pressures typically encountered in a particle-size reduction apparatus. Typically, a high-pressure seal can withstand pressures of up to 5,000 psi, preferably up to 10,000 psi, more preferably up to 20,000 psi, and in a particular embodiment, up to 30,000 psi.

The invention further provides an annular high-pressure seal, for a plunger reciprocating within a barrel, comprises lower and upper body portions, said upper portion being in the form of a cup and having sides surrounding a recess, the sides being outwardly deformable so that respective outer and inner edges of the sides of the cup make, in use, sealing contact with respectively the barrel and the plunger, the seal further comprising a brace to prevent the sides from collapsing into the recess under low pressure and wherein the seal is sterilisable.

By 'sterilisable' it is meant that sterility sufficient to satisfy MCA and FDA regulations for pharmaceutical use (as outlined above with relation to sterility of the particle-size reduction apparatus) is achieved.

The seal of the invention confers the advantage that it can be sterilised, an especially important feature as the seal comes into contact during operation of the apparatus with suspension on the high pressure side of the apparatus. We have found that prior art seals contain structural and surface features that harbour microorganisms, rendering these known seals incapable of sterilisation, and these features are avoided in the seal of the invention.

In a preferred embodiment, the brace of the plunger seal presents a smooth surface free from cavities. By free from cavities it is meant free from holes, cracks, gaps or other spaces in the otherwise solid mass of the brace. Minimising (and preferably eliminating) cavities in which microorganisms may collect, ensures that complete sterilisation of the seal can take place.

It is further preferred that the resilient plastics material is disposed in the recess between the cup sides of the plunger seal. The plastics material can fill the recess of the plunger seal so that the upper surface of said plastics material is level with or nearly level with the height of the cup sides, i.e. the upper surface of said plastics material reaches at least two thirds the height of the cup sides.

The plunger seal may further comprise a metal spring; if so this is preferably enclosed within the resilient plastics material of the brace. Using a metal spring adds further strength or resilience to the brace of the seal, and enables choice of alternative plastic materials for the brace.

Usually, the plunger seal is operable at temperatures up to 75° C., preferably at temperatures up to 90° C., most preferably at temperatures required for sterilisation of the apparatus, generally up to about 122° C. The plunger seal material may be virgin PTFE or glass-strengthened PTFE. These materials are known to be capable of withstanding high pressures and temperatures without extruding. An example of glass-strengthened PTFE from which seals of the invention can be made is Rulon(®).

It is preferred that the plunger seal brace is manufactured from a different material to that of the other seal components, so that the cup sides of the seal will deform outwardly under the high pressures experienced during operation of the apparatus and form sealing contact with the plunger and the bore but nevertheless so that under low pressure, e.g. whilst the machine is at rest, the cup sides do not collapse inwardly leading to subsequent seal failure. The resilient plastics material of the brace is preferably more flexible then the material of the upper and lower body portions of the seal. It is, however, an option for the brace to be manufactured from the same material to that of the other seal components, so long as the seal remains outwardly deformable in use.

Preferred apparatus of the invention and component parts therefor are hence substantially free of niches which can harbour microorganisms and/or their spores or which can shield them from the effects of the sterilising steam and/or water during sterilisation of the apparatus and its parts. For example, the apparatus preferably avoids unnecessary pipework or pipework containing dead-ends or inaccessible spaces that would represent such niches and compromise sterility or validation thereof. Other adaptations enable access of sterilising steam or water to parts of the apparatus which might otherwise harbour microorganisms or spores.

The present invention further provides methods of sterilising a particle-size reduction apparatus. A first method comprises the step of charging the particle-size reduction apparatus of the invention with steam, to achieve sterilisation.

A sterilisation protocol may optionally be followed by a method of validating sterilisation—in order to ensure that the sterilisation is effective and/or complete. In a particular embodiment of the present invention, sterilisation is deemed to have occurred when a protocol, previously demonstrated to achieve a 6 log reduction in heat resistant bacterial spores is followed.

Generally, validation of sterility is carried out in order to establish a protocol which is demonstrated to result in a sterile apparatus, which apparatus is then used to reduce the particle size of a sterile suspension. Validation of sterility is not then routinely carried out with every batch, but may be used as part of regular maintenance of the apparatus or to carry out spot checks on individual batches of suspension.

When sterilising the particle-size apparatus using steam, it has been found advantageous to insulate the valves and conduits downstream of the interaction chamber, so as to maintain steam temperature during sterilisation. Loss of heat from the steam can cause undesirable condensation and loss of effective sterilisation.

Referring to a specific embodiment of the invention, described in more detail in the examples, steam traps are used around the apparatus, located in places where condensate would develop and risk accumulating. The steam traps are open when the temperature is below 121° C. but during sterilisation the traps are open until they have reached the sterilising temperature, generally 121° C., at which point they close. If the temperature in a trap drops, for example due to accumulation of condensate, the trap opens, releasing the condensate from the apparatus, and then will close again when the temperature has reached 121° C. Thus during sterilisation, traps are continually opening and closing.

Temperature probes are used all around the apparatus to provide a temperature map of the apparatus and to confirm that the temperature in all relevant places is at least 121° C. The probes are connected to a central monitoring unit, so that the duration of the sterilisation procedure is timed from the point at which all relevant parts of the machine have reached the sterilising temperature.

During sterilisation the following steps are typically carried out:
steam traps are connected;
temperature monitors are connected;
steam is introduced into the apparatus, optionally with the apparatus running;

temperature is monitored at each monitor until all have reached the sterilising temperature, generally 121° C.;
during this period, the steam traps start in the open position but close as they reach 121° C., opening and closing as described above;
the time at which temperature recorded by each of the temperature monitors has reached the sterilising temperature is noted;
once all monitors have reached 121° C. then the sterilisation is continued by continuing to introduce steam into the apparatus for a predetermined period of time this time being determined empirically.

The number of steam traps connected to the apparatus varies with the type of apparatus and depends on the particular sterilisation protocol being carried out. We have achieved good results using an M-210EH Microfluidizer(®) with up to 20 steam traps, but it is an option to use fewer steam traps, for instance up to 10, but preferably at least 5 steam traps are used.

The number of temperature monitors connected to the apparatus varies with the type of apparatus used. We have achieved good results using an M-210EH Microfluidizer(®) with up to 10 temperature monitors, though it is an option to use fewer temperature monitors, for instance about 5 temperature monitors, or more temperature monitors, for instance, up to 20.

When the apparatus is allowed to run during introduction of steam, the apparatus is run at a slow speed. When an M-210EH Microfluidizer(®) is used, steam is introduced at a speed of typically up to half the running speed of the apparatus, and in some embodiments, up to a third of the running speed of the apparatus.

In a particular embodiment, this period is determined by introducing heat resistant bacterial spores into the apparatus, introducing steam into the apparatus and monitoring apparatus temperature until it has reached the sterilising temperature; continuing to introduce steam for a first known amount of time; determining whether after that first known amount of time sterilisation has been achieved; and if sterilisation has not been achieved, repeating the method for a second, longer known amount of time.

In practice, a protocol is determined that is accepted as ensuring sterilisation after a given period of time, and this time is noted and a margin of error, such as an additional at least 5, 10 or 20 percent of the noted time, is added and this modified protocol is noted as the sterilising protocol. Also in practice, the intensifier tends to take longest to reach an acceptable sterilising temperature. The intensifier can be provided with a jacket or other insulation to help speed up this process.

During sterilisation, it is preferred that all steam exiting the intensifier passes through the interaction chambers—i.e. sterilising steam cannot bypass the interaction chambers, as this may risk creation of areas in the apparatus, around the chambers, which cannot be sufficiently reached by the steam to achieve sterilisation. A jacket is also optionally located around the interaction chambers. This jacket can be used to increase the temperature of the interaction chambers using steam to assist sterilisation and it can be used to cool the interaction chambers when the machine is operated.

Whilst sterilising the apparatus described in the examples, as steam is passed through the chambers it passes from a 3 mm diameter feed to a 0.087 mm feed, potentially resulting in some condensation which is trapped at the interaction chamber exit. It is thus preferred that steam is introduced into the intensifier and, in addition, downstream of the interaction chamber or chambers, this step assisting in rapid sterilisation of apparatus, conduits etc, located the other side of the interaction chambers from the primary steam source. The problem of condensation at the interaction chamber exit can also be reduced by pre-heating the interaction chambers.

A second method comprises charging the particle-size reduction apparatus of the invention with pressurised, superheated water so as to sterilise the apparatus.

When pressurised, superheated water is used for sterilisation, the intensifier can be operated so as to control the temperature of the water during sterilisation. Operating the intensifier leads to an increase in the pressure of the water within the apparatus, in turn leading to an increase in temperature which can be monitored. Hence, by adjusting pressure within the apparatus, temperature within the apparatus can also be adjusted and kept at or above a desired sterilising temperature of 121° C. Following a preferred embodiment of the water-based sterilisation method, water is introduced into the apparatus at a temperature below 100° C., and this could suitably be at room temperature, and the apparatus is then operated so as to increase the water temperature up to the desired sterilising temperature. Temperature monitors located on the apparatus are used to confirm that the desired temperature has been reached, at which point sterilisation is continued at or above this temperature for a time period previously determined to be accepted as resulting in sterilisation, this time period being determined empirically.

When pressurised, superheated water is used for the sterilisation method, it is preferred that steam is nonetheless used for sterilisation of the isolation area of the intensifier, and the method comprises charging the isolation area of the intensifier with steam, at a temperature the same as or higher than the temperature of the water, preferably at least 0.5° C. higher.

After sterilisation has been carried out, the water is cooled and, for example, Budesonide suspension and optional extra ingredients such as surfactants are added. One option is to sterilise the apparatus using super-heated water, then use sterile air to flush the system and then introduce a Budesonide suspension. Another option is to sterilize the apparatus using super-heated water containing surfactant, cool the water and surfactant solution and then add the Budesonide suspension. In this way, the end of the sterilising step becomes the beginning of the priming step. Further, a filter can be used to collect microorganisms.

The present invention further provides a method of preparing a sterile suspension, in particular a sterile suspension comprising Budesonide or Fluticasone, comprising the steps of obtaining a sterile particle size reduction apparatus, passing a sterile suspension through the sterile apparatus, and monitoring particle size in the suspension. Preferably, the particle size reduction apparatus is sterilised according to the steam or water sterilisation methods of the present invention, as described above. In one embodiment, particle size in the suspension is monitored continuously as the suspension is passed through the apparatus. In another embodiment, particle size is monitored between discrete passes. The suspension is passed through the apparatus until the desired final mass median diameter of the particles is obtained—typically 2-3 μm. Once the desired particle size has been achieved, the sterile suspension may then be transferred from the apparatus to be packaged into sterile ampoules, preferably nebules.

In another aspect, the present invention also provides a sterile nebule containing a sterile suspension prepared according to the present invention. When the suspension in the nebule comprises Budesonide or Fluticasone, the sterile nebule may be of use in the treatment of asthma or chronic obstructive pulmonary disorder.

As described above, there are numerous problems associated with conventional methods for removing a seal from a bore and for inserting a seal into a bore. For example, there is a large potential for human error and consequent damage to the seal when conventional methods are used. Furthermore, the conventional methods cannot be used to validate the sterility of the particle-size reducing apparatus.

Hence, the present invention provides a seal retractor, comprising a shaft and at least one projection moveable between a first and a second position, wherein said first position is for insertion of the seal retractor into a bore containing a seal, and said second position is for removing the seal from the bore.

The seal retractor of the present invention has the dual functions of a) enabling easy and accurate insertion and removal of the seal and b) minimising contamination of the seal, thus facilitating validation of apparatus sterility. Importantly, the device can position the seal at exactly the right place in the barrel for its function, and achieve this without damaging either the seal or the bore. It is advantageous to prevent damage such as scratching to the bore in order to ensure sterility of future runs, since any scratches provide niches in which micro-organisms may collect.

The seal retractor of the present invention is very quick, clean and easy to operate, allowing quick turn-around of seals by semi-skilled operators. A particular advantage of the present seal retractor is that it enables very precise placement of the seal components every time and all the seal components are inserted into the apparatus barrel together. Hence, the likelihood of incorrect placement of the seal is much reduced in comparison to the conventional method.

When removing and inserting a seal according to the present invention, damage to the seal and/or the bore of the barrel is greatly reduced, and preferably avoided altogether. Hence, the present seal retractor can advantageously be used for maintenance and validation purposes. By reducing the likelihood of damage to the seal when it is inserted into the barrel, the chances of system failure during a subsequent run are greatly minimised. By reducing the likelihood of damage to the seal when it is removed from the barrel, it can be easily ascertained whether damage has occurred to the seal during use. By reducing the likelihood of damage to the bore, sterility of the apparatus for future runs can be ensured.

A preferred seal retractor of the invention is designed specifically for inserting seals into and removing seals from the bore of a plunger barrel of particle-size reduction apparatus described above and in the specific embodiment, especially designed for Microfluidizer(®) model M-210EH. The principles of the seal retractor are nevertheless believed to be applicable generally to insertion and removal of seals in or from a particle-size reduction apparatus generally.

In a preferred embodiment of the invention, the projection or projections is or are located at the terminus of the seal retractor—i.e. at the terminus of the shaft. In said second position, the projection is projected and in said first position, the projection is retracted. By projected it is meant that the projection extends beyond the diameter of the terminus of the seal retractor shaft so that it is capable of contacting the seal. By retracted it is meant that the projection does not extend beyond the diameter of the terminus of the seal retractor shaft and it is not capable of contacting the seal.

The moveable projection or projections may generally be of any size or shape, and may be of any number. Where there are a plurality of projections, these may be moveable independently or in concert.

The retractor is preferably adapted for use with the seal of the present invention, and thus with the projection in the first position—i.e. the retracted position—the seal retractor can be inserted through the seal, and with the projection in the second position—i.e. the projected position—the retractor can exert a pulling force on the seal, to pull a seal out of a bore.

Optionally, in said second position, the moveable projection or projections secure the seal onto the seal retractor, enabling the seal to be easily removed from a bore, attached to the seal retractor.

It is preferred that, in said second position, the moveable projection does not project beyond the lip of the seal, and thus damage to the bore (such as scratching by the projection) is reduced and preferably avoided.

The moveable projection or projections may be connected to control means to enable remote control of said projection or projections between said first and second positions. In a particular embodiment, said control means comprise a rotatable knob and rotating said knob causes the moveable projection or projections to rotate between the first and second positions. Hence, whether the projections are in the projected or retracted position may be controlled remotely. This is advantageous because manual contact with the seal and bore is minimised and preferably avoided, thus reducing damage to or contamination of the seal and apparatus. The rotatable knob may be located at the opposite end of the shaft to the moveable projection or projections and connected thereto via a connecting rod.

When it is required to insert a seal into or remove a seal from a bore of a particle-size reduction apparatus, the seal retractor may be attached to the apparatus by any suitable means, for example, the seal retractor may be screwed onto the end of the plunger barrel of the particle-size reduction apparatus.

The present invention also provides a method of accurately positioning a seal into a bore using the seal retractor of the invention. The invention further provides a method of removing a seal from a bore using the seal retractor—which method can also be used for validating sterility of a bore.

The present invention also provides a method of inserting a seal into a bore, such as the bore of a plunger barrel of a particle-size reduction apparatus and particularly a Microfluidizer(®) M-210EH apparatus. The method comprises securing a seal to the seal retractor with said at least one movable projection in the second position and inserting said seal retractor into said bore, and thereby accurately positioning the seal into the bore. Use of the seal retractor means that the possibility of inserting the seal into the bore incorrectly is greatly reduced in comparison to when prior art methods are used.

The method preferably further comprises the step of moving the moveable projection or projections to the first position—i.e. the retracted position—and thus releasing the seal from the seal retractor. This enables the seal retractor to be removed from the bore without the seal, leaving the seal in situ.

According to a particular embodiment of the present invention, the seal components may be placed onto the terminus of the shaft of the seal retractor and secured by turning the projection or projections to the second, projected position. In order to avoid scratching the bore, the projections do not extend beyond the lip of the seal when projected. The seal retractor is then attached onto the barrel of a particle-size reducing apparatus and the shaft is lowered, optionally by means of a handle, thus lowering the seal into the barrel to the desired position. The seal is released from the seal retractor by turning the projections to the first, retracted position and then the shaft is raised and the seal retractor is removed from the barrel, leaving the seal in situ.

The present invention further provides a method of removing a seal from a bore, such as the bore of a plunger barrel of a particle-size reduction apparatus, comprising inserting a seal retractor into the bore, with the moveable projection or projections in the first position, moving the projection to the second position, and then removing the seal retractor from the bore, thereby removing the seal from the bore. This method is typically carried out under sterile conditions, to avoid contamination of the seal once it is removed from the bore. If sterility of the seal is maintained during the removing process then the seal can subsequently be used to validate sterility of the bore.

According to a preferred embodiment of the present invention, the seal retractor is attached to the plunger barrel with the projection or projections in the retracted position. The shaft of the seal retractor is lowered into the barrel, optionally using a handle, so that the terminus of the seal retractor shaft is inserted within the seal. The projection or projections are moved to the projected position to contact the lips of the seal and then the seal is raised out of the barrel on the end of the seal retractor shaft. The seal can then be removed from the end of the seal retractor by moving the projections to the retracted position.

The sterility of a bore may then be validated by the following method, which is carried out under sterile conditions. The method comprises the steps of removing a seal from the bore, under sterile conditions transferring the seal to growth medium, observing whether there is growth of microorganisms in the growth medium, calculating the number of microorganisms present, and thereby determining whether the bore is sterile. In a preferred embodiment, the method comprises the initial steps of inoculating the seal with a known quantity of heat-resistant bacterial spores, most preferably at least $1 \times 10^6$ heat-resistant bacterial spores, inserting the seal into the bore, and carrying out a sterilisation protocol as described above.

Sterility is judged according to the MCA and FDA guidelines. The seal is typically incubated in the growth medium under conditions conducive to growth of microorganisms, and growth of microorganisms indicates that the seal (and hence the bore) has not been sterilised effectively. In a preferred embodiment, the validation method comprises the steps of inserting a seal inoculated with a known number of heat resistant bacterial spores into the bore, carrying out a procedure intended to sterilise the bore, and then validating sterility of the seal, and hence the bore. The bore may be the bore of a particle-size reducing apparatus and, in one embodiment, the sterility of the bore may be used as an indication of sterility of the entire apparatus.

The invention is now described in more detail with reference to the accompanying drawings, in which:

FIG. 1 is a schematic diagram showing flow of suspension between the component parts of a particle-size reduction apparatus;

FIGS. 2, 3 and 4, respectively are front, top and side views of a Microfluidizer(®) M-210EH apparatus modified according to one embodiment of the present invention;

Figure 20:
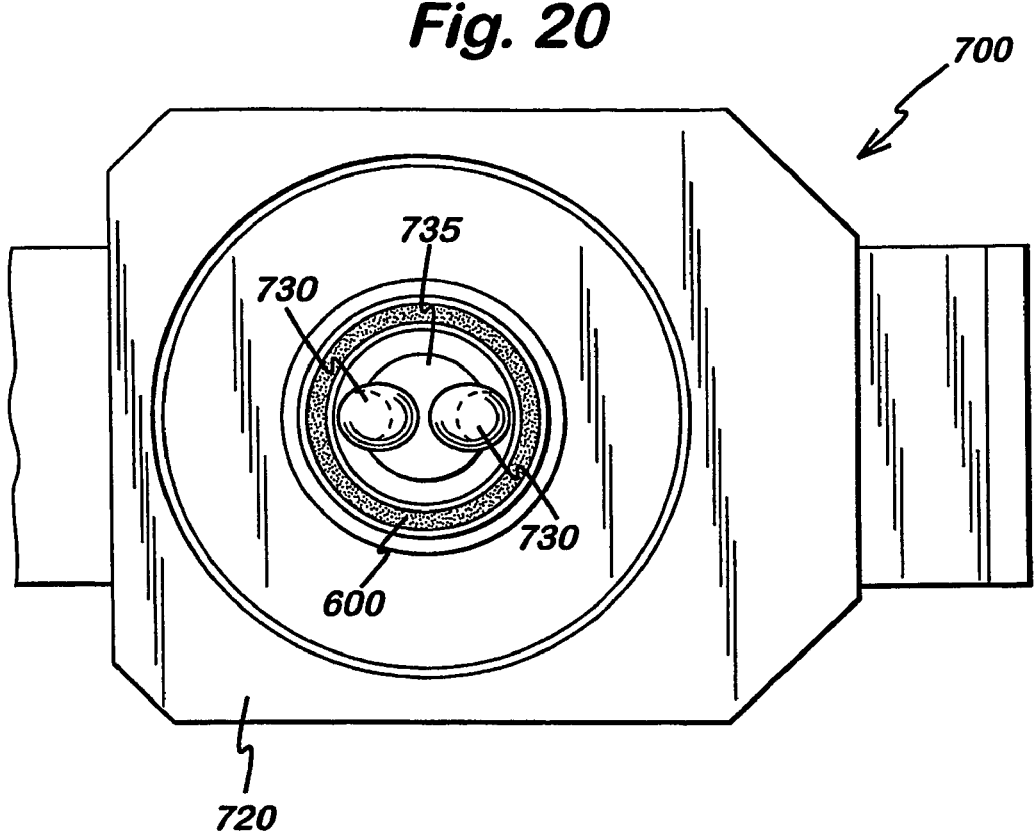
Figure 21:
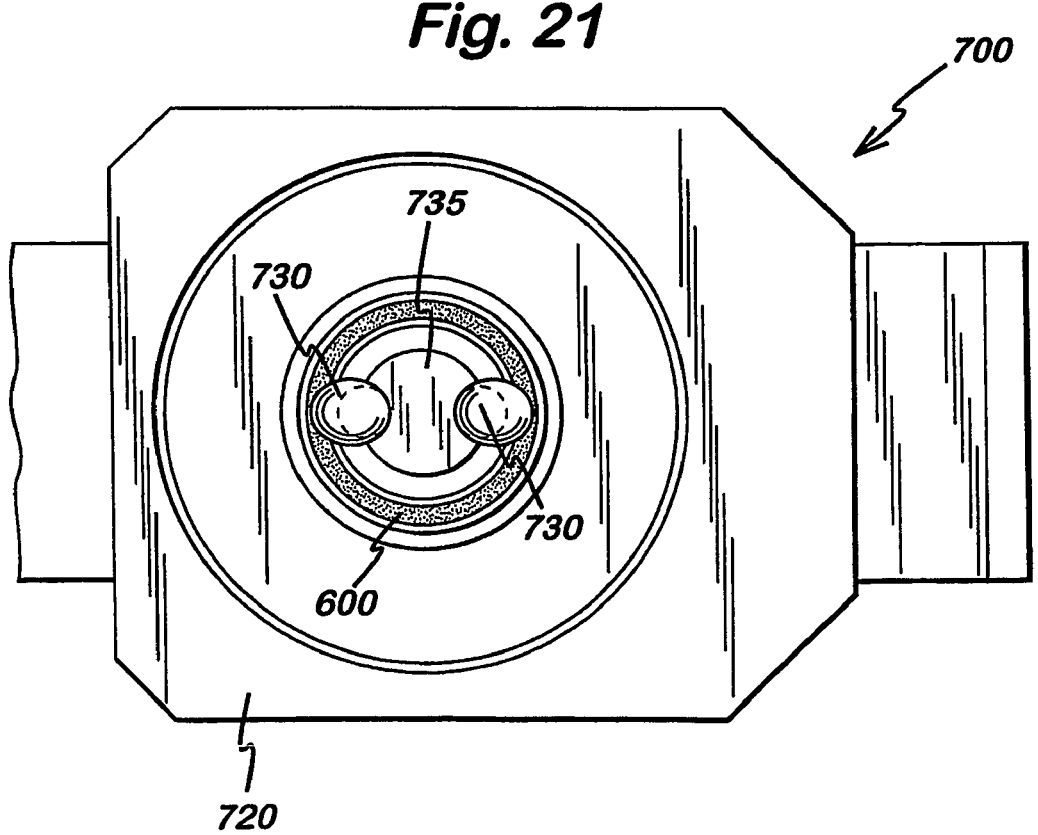
Figure 22:
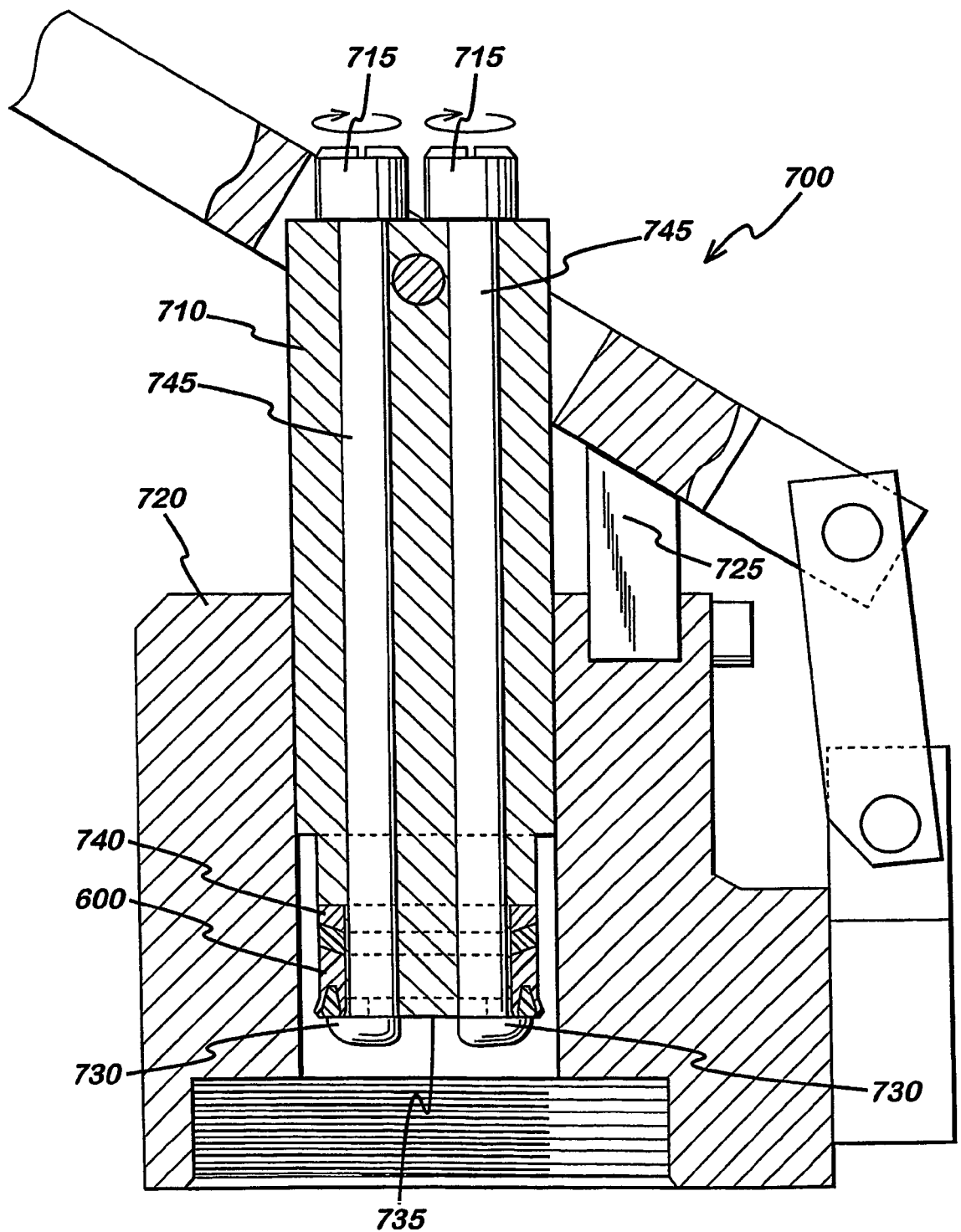
Figure 23:
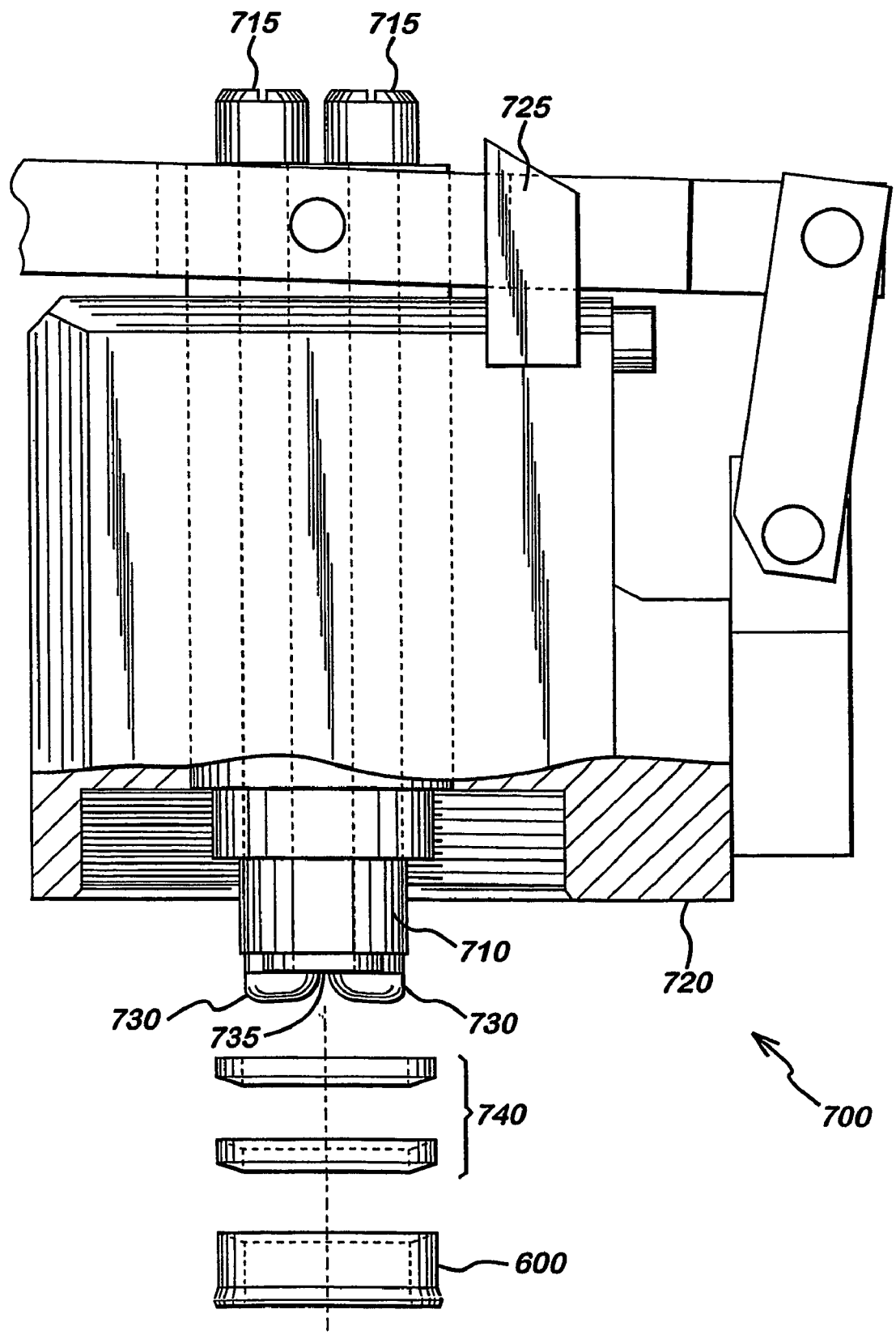

In FIGS. 20 and 21, a seal according to one embodiment of the present invention is attached to the end of the shaft terminus; and FIGS. 22 and 23 are, respectively, a cross-sectional and part cross-sectional view of a seal retractor according to one embodiment of the present invention. A seal according to one embodiment of the present invention is attached to the end of the shaft terminus in FIG. 22 and the seal components are shown in expanded view below the shaft terminus in FIG. 23.

Figure 1:
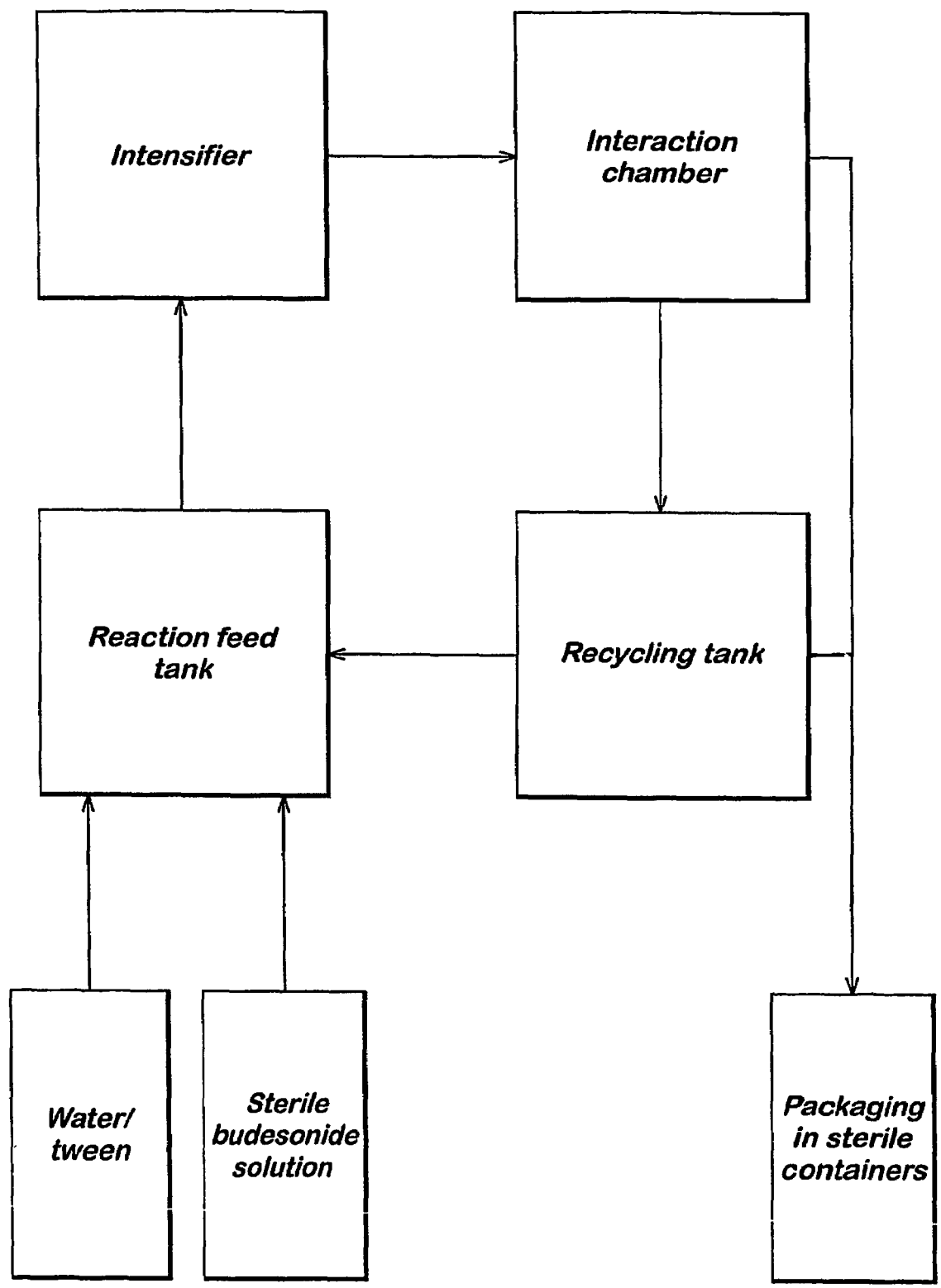
Figure 2:
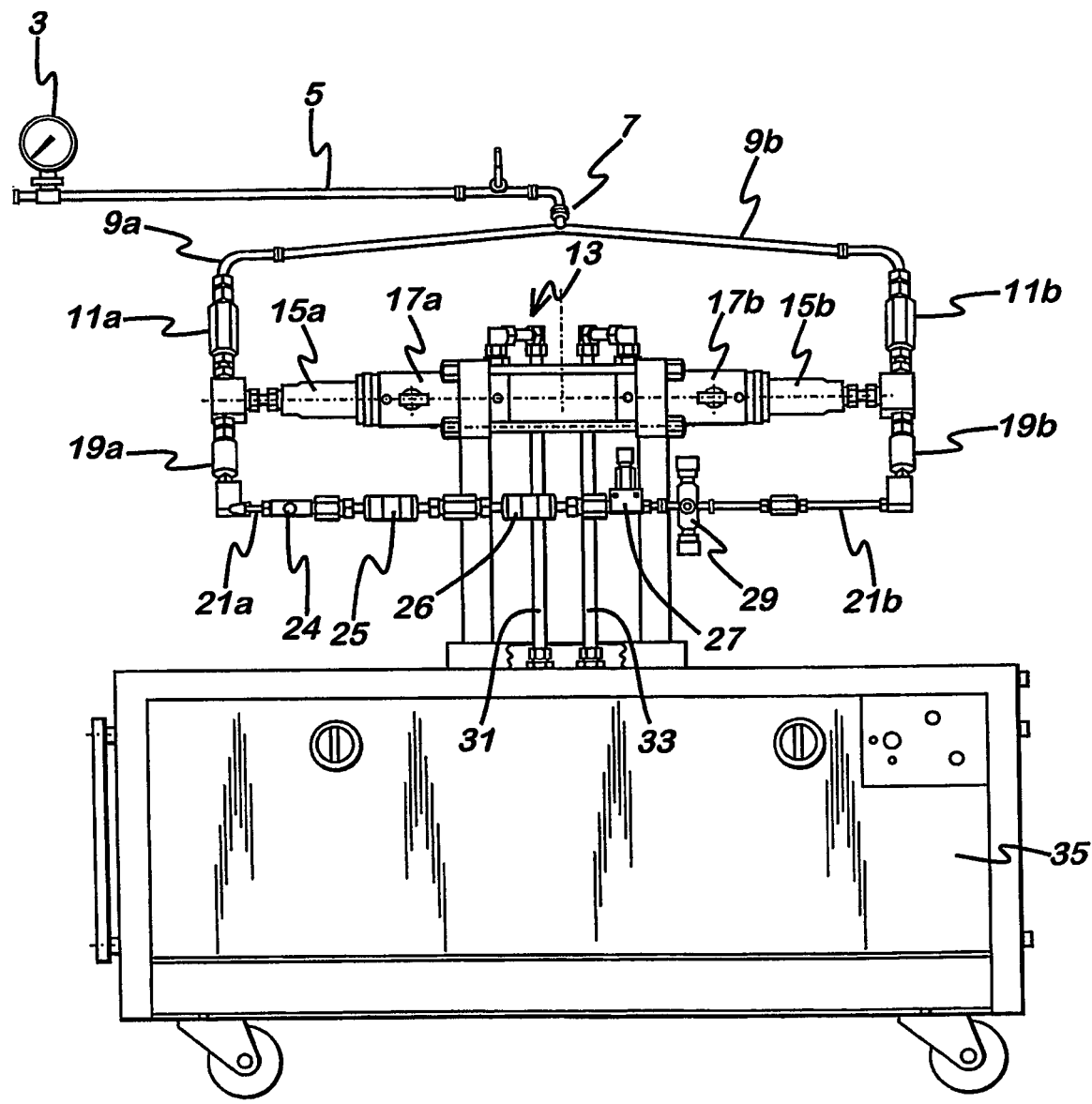
Figure 3:
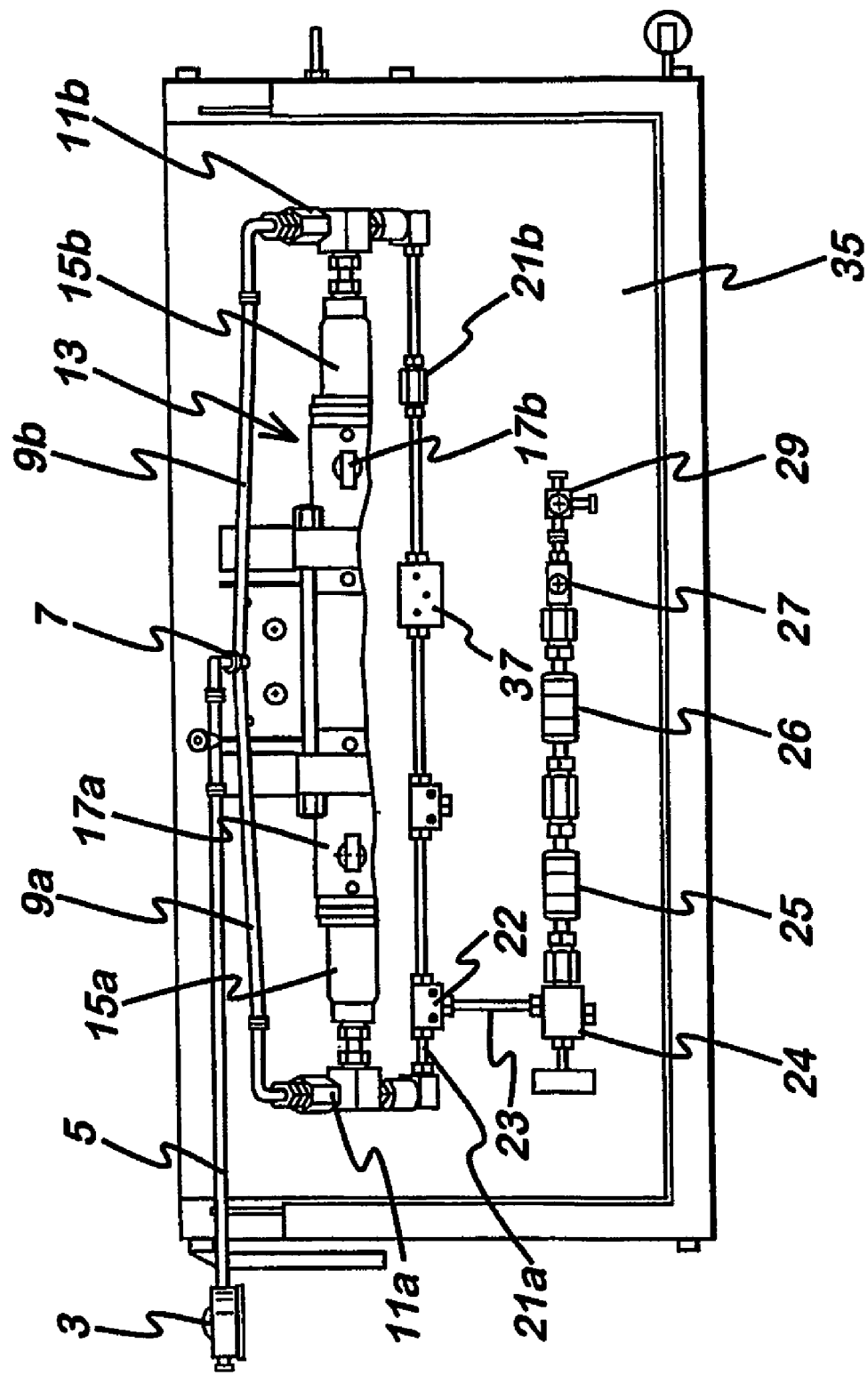
Figure 4:
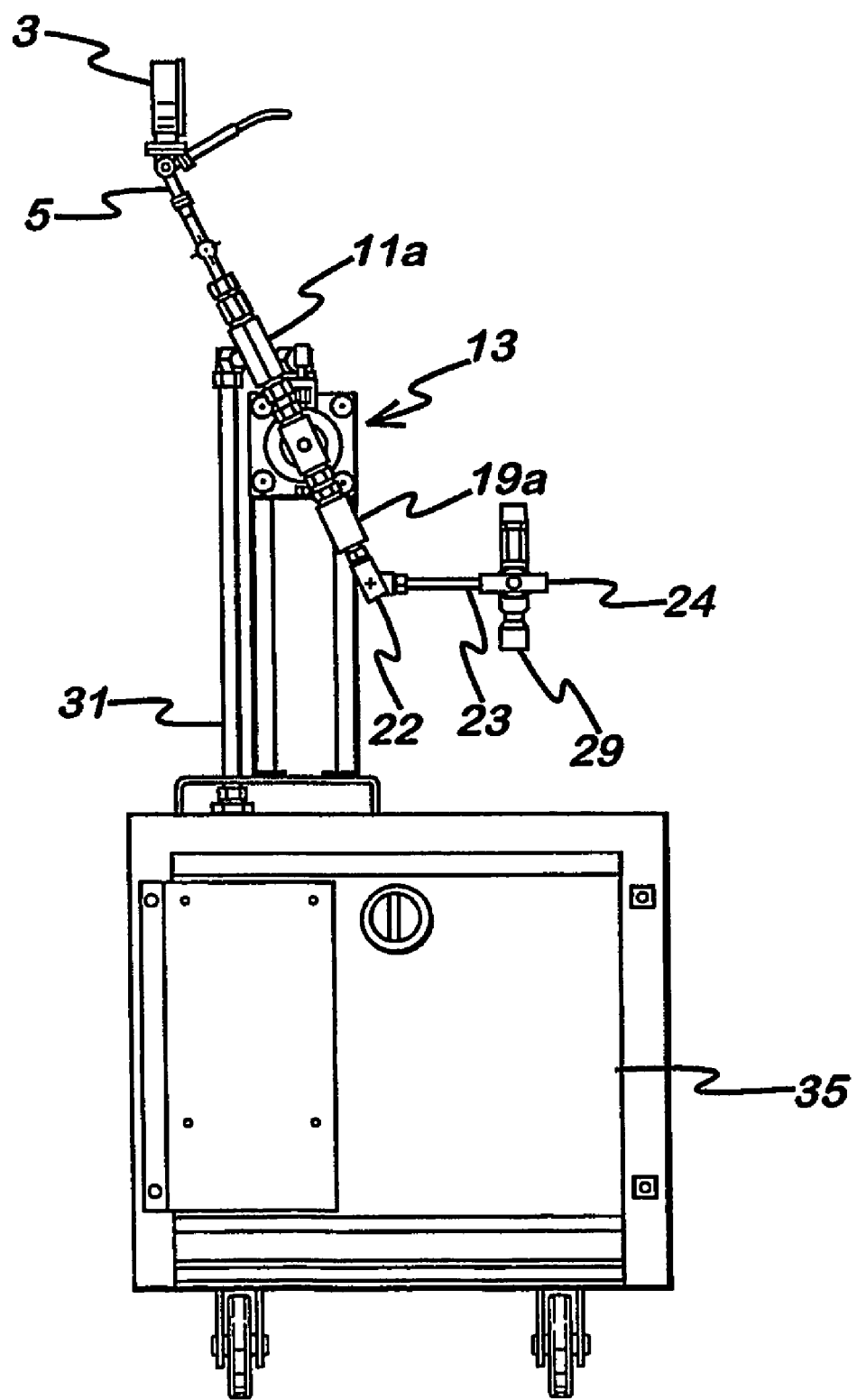

Referring to the drawings in more detail, FIG. 1 is a schematic diagram showing flow of a sterile Budesonide suspension between the main component parts of the particle-size reduction apparatus. The suspension is generated in the reaction feed tank—by combining a sterile solution of Budesonide in alcohol with an aqueous solution comprising Tween and water. The sterile suspension is fed into the intensifier of the apparatus from the reaction feed tank via a conduit. The output from the intensifier leads, via a conduit, into the input of the interaction chamber. The interaction chamber has two outputs and hence, from the interaction chamber, the suspension may follow either of two routes. If particle size has been reduced to the desired final mass median diameter, the suspension leaves the apparatus for packaging in sterile containers, such as ampoules. If, however, particle size is still too large, the suspension leaves the interaction chamber and passes via a conduit into the recycling tank. The recycling tank then feeds the suspension back into the reaction feed tank, from which the suspension is fed back into the intensifier for another pass. Alternatively, product can be transferred from the recycling tank to be further processed and/or packaged.

As can be seen from FIG. 1, the suspension cannot pass from the output of the intensifier to the input of the intensifier without passing through the interaction chamber, because there is no conduit between the output of the intensifier and the input of the intensifier other than via the interaction chamber.

In practice, the particle-size reduction apparatus is run in almost discrete passes. Suspension from the interaction chamber that must be passed through the apparatus at least once more is fed into the recycling tank and accumulates there whilst the reaction feed tank empties. Only once the reaction feed tank is almost empty is suspension from the recycling tank fed back into the reaction feed tank for another pass.

A Microfluidizer(®) M-210EH particle-size reduction apparatus (1) modified according to one embodiment of the present invention is now described with reference to FIGS. 2-5. FIG. 2 shows a front view of the modified apparatus, FIG. 3 shows a top view and FIG. 4 shows a left side view.

The Microfluidizer(®) comprises intensifier (13), interaction chambers (25 and 26) and base unit (35) housing an oil tank, pump and motor (not shown).

Sterile suspension enters the Microfluidizer(®) from the reaction feed tank via input (3) and passes along conduit (5). At T-junction (7) the flow of suspension is split along two conduits (9*a* and 9*b*), which feed into opposite ends of the symmetrical intensifier (13) via non-return valves (11*a* and 11*b*). The non-return valves prevent the suspension from flowing back along conduits 9*a* and 9*b*, which might otherwise result due to the high pressures created in the intensifier.

Suspension passes into the plunger barrels (15*a* and 15*b*) at each end of the intensifier. Suspension is prevented from entering the isolation chambers (17*a* and 17*b*) by plunger seals (not shown on FIGS. 2-4).

Each M-210EH series machine contains an on-board 15 horsepower electric-hydraulic module within base unit (35) that provides power to a double-acting intensifier plunger (not shown on FIGS. 2-4). The intensifier plunger amplifies the hydraulic pressure and, in turn, imparts that pressure to the product stream. The intensifier typically has a multiplier ratio of about 3:1 to 20:1. Process pressures ranging from 2,500 to 30,000 psi may be selected.

The intensifier plunger supplies the desired high pressures at a constant rate to the product stream. As the plunger travels in one direction, it drives the suspension at constant pressure through the channels in interaction chambers (25 and 26). As the intensifier plunger continues its travel in one direction, a series of check valves allow suspension to be drawn into the opposite end of the pump barrel. Oil lines (31 and 33) provide a flow of oil within the plunger barrels that regulates the direction of movement of the plunger within each plunger barrel. Thus, as the intensifier plunger completes its stroke, it reverses direction and the new volume of suspension is pressurized repeating the process. This creates a constant flow of suspension at near constant pressure through the interaction chamber.

Suspension at high pressure leaves each plunger barrel 15*a* and 15*b* of the intensifier via non-return valves (19*a* and 19*b*) respectively, and passes along conduits (21*a* and 21*b* respectively). A pressure transducer (37) on conduit 21*b* monitors pressure of the suspension as it passes along conduit 21*b*. Once the two flows of suspension along conduits 21*a* and 21*b* reach T-junction (22), the flows are combined in conduit (23).

From conduit 23, the pressurised suspension enters the interaction chambers (25 and 26) via diaphragm needle valve (24). It is within the interaction chambers that particle-size reduction occurs, as the suspension is forced through precisely defined fixed-geometry microchannels in the interaction chambers under high pressure (up to 30,000 psi) creating shear and impact forces as the product stream impinges upon itself and on wear-resistant surfaces at ultra-high velocities. The channels in the first interaction chamber (25) are of pore diameter 400 μm and the channels in the second interaction chamber (26) are of pore diameter 78 μm. The combined forces of shear and impact within the microchannels act upon products to reduce mean particle size (mass mean diameter) and can reduce the mean particle size of a Budesonide suspension from approximately 50 μm to 2-3 μm in 14-20 passes through the Microfluidizer at 22,000 psi.

Downstream of the interaction chambers there is a rupture disc (27), which bursts at 150 psi in the event of a build up of pressure caused by a blockage in the apparatus pipework.

Suspension leaves the interaction chamber via outlet (29). The outlet may be connected to a conduit for returning suspension that has not yet reached the desired particle size to the recycling tank (not shown) ready for another pass through the Microfluidizer(®). The machine operates comfortably at 1.2 liters per minute at an operating pressure of 20,000 psi. A typical batch is 12 liters, and is passed 14 times through the apparatus, taking 140 minutes to process at this rate.

Alternatively, if the mass median diameter of particles in the suspension has reached the desired particle size, the suspension may be fed from outlet (29) into the recycling tank before being diluted, mixed with other excipients and transferred to a means for sterile packaging (not shown), for example into sterile ampoules.

Figure 5:
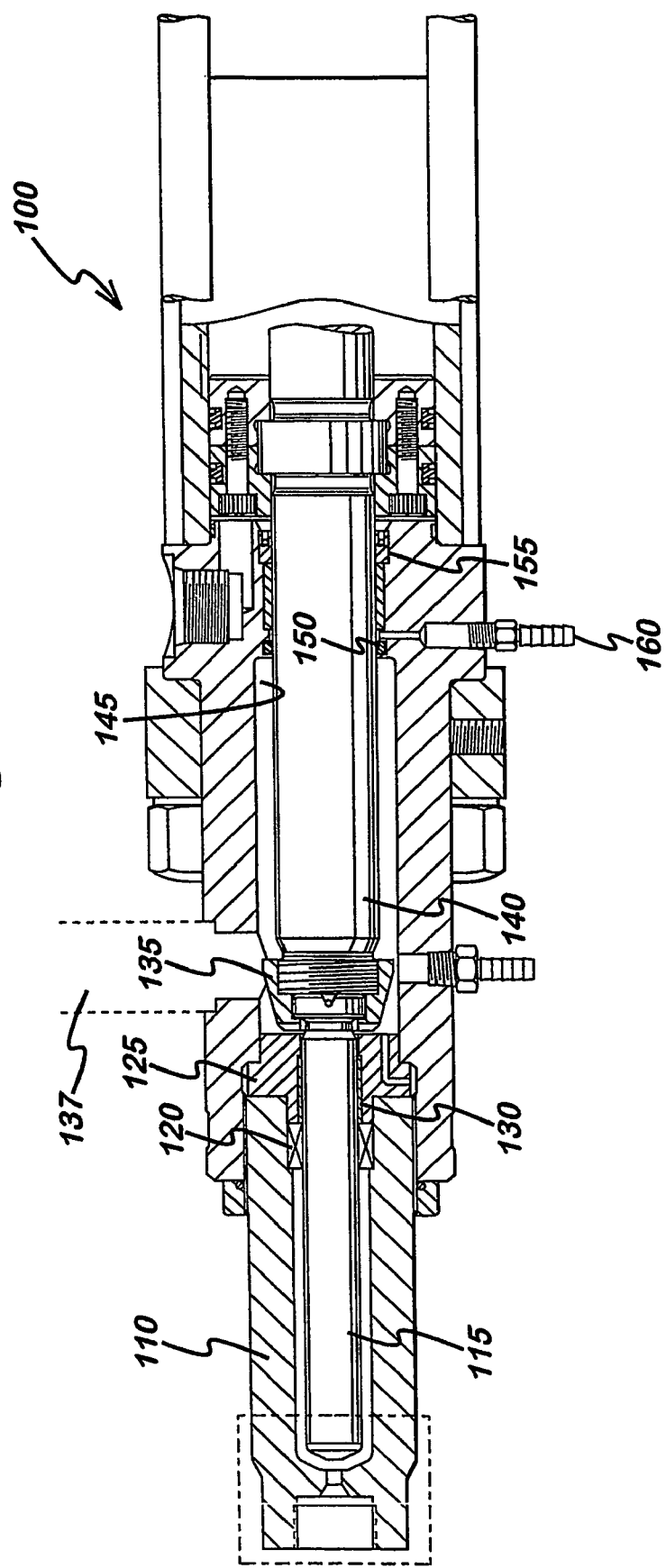
FIG. 5 is a cross-sectional view of the intensifier of a Microfluidizer(®) M-210EH apparatus modified according to one embodiment of the present invention.

FIG. 5 shows a cross section of the left hand side of the intensifier part (100) of the modified apparatus. The following description of the left-hand side of the intensifier applies also to the right-hand side, since intensifier is symmetrical.

The intensifier comprises two main sections—plunger barrel (110) and isolation chamber (145). A plunger (115) is housed in the plunger barrel (110) and is connected via cam nut (135) to a connecting rod (140), which is located in the isolation chamber (145). The cam nut (135) is screwed tightly onto the end of connecting rod (140) but plunger (115) is held loosely in position by cam nut (135).

Cam nut (135) interacts with an air switch (not shown but located in the position surrounded by dotted lines (137)) which controls direction of movement of plunger (115) within plunger barrel (110). As plunger (115) is driven inwards within the plunger barrel, cam nut (135) approaches and then hits and triggers the air switch, changing the direction of flow of oil from the oil lines to the plunger around connecting rod (140) and forcing the plunger back in the reverse direction. The oil pressure used is up to 5,000 psi, resulting in up to 30,000 psi of pressure inside the plunger barrel.

The plunger barrel is isolated from the isolation chamber via a plunger seal located in seal location (120). The plunger seal (shown in detail in FIGS. 14 and 15) prevents flow of suspension from the plunger barrel to the isolation chamber in use and is designed to withstand the high pressures (up to 30,000 psi) generated within the plunger barrel.

Between the plunger seal and the cam nut (135) is a bushing (130) supported within bushing housing (125). The bushing supports the plunger (115) as it reciprocates within the plunger barrel.

The back of the isolation chamber (145) is provided with two oppositely facing seals (150 and 155). Seal (155) retains oil used to drive the connecting rod, whist if there is any leakage of this oil the second seal (150) ensures it passes into drain (160). The main purpose of seal (150), however, is to prevent suspension from interfering with the hydraulic pump section of the apparatus in the event of failure of the plunger seal. Seal (150) is a lip-type seal, made from PTFE, and is capable of withstanding pressures of 150 psi at 200° C. while the plunger is moving.

Figure 6:
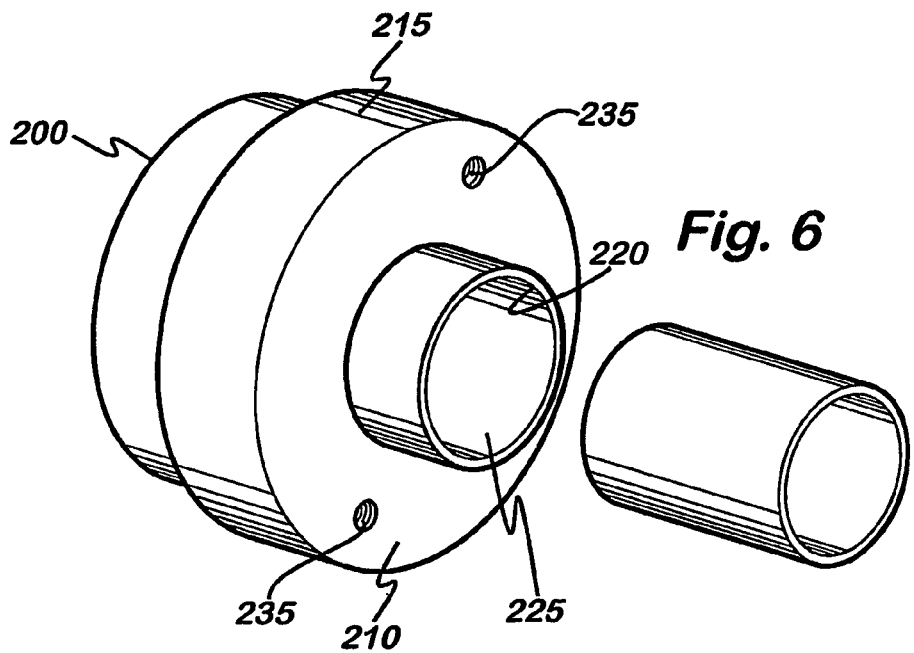
FIGS. 6 and 7 are isometric views of a bushing holder modified according to one embodiment of the present invention, together with a prior art bushing.
Figure 7:
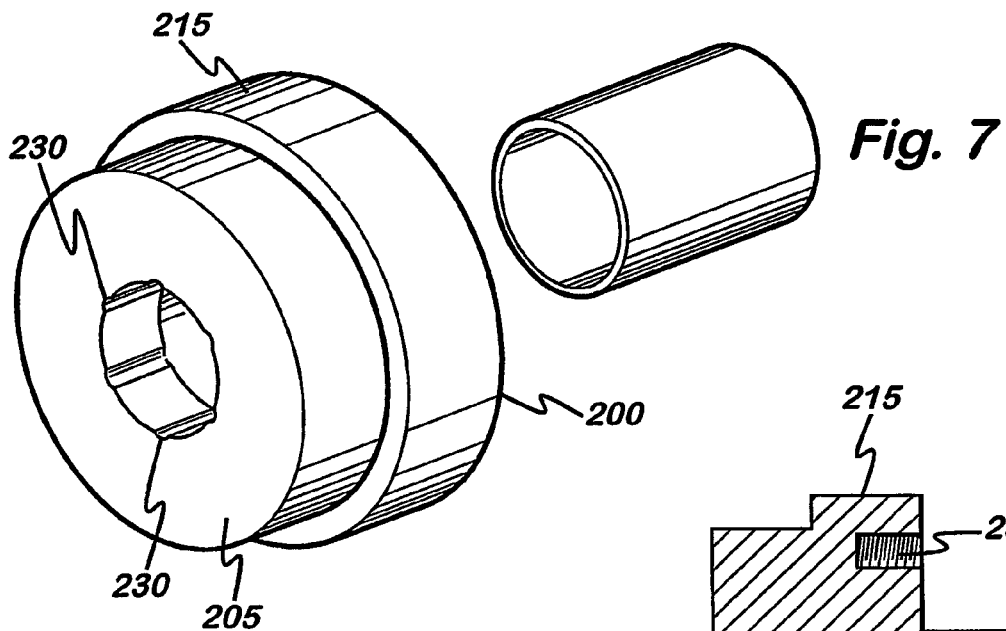
Figure 8:
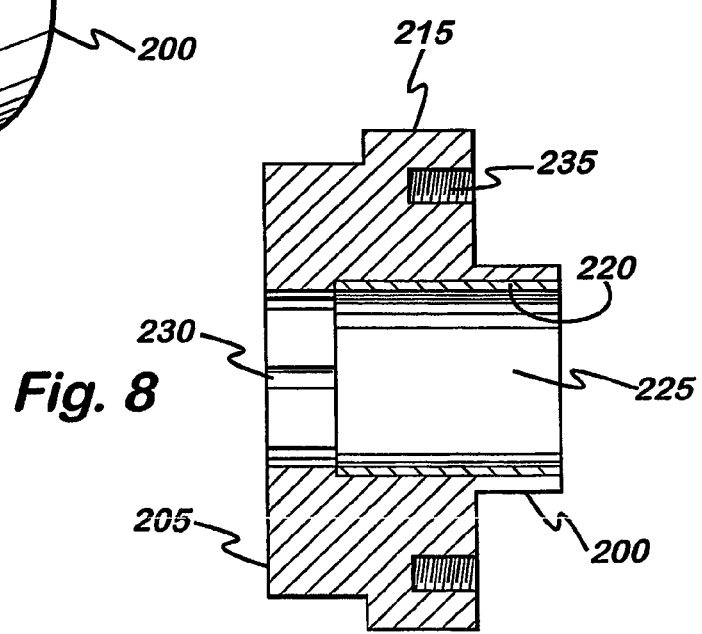
FIG. 8 is a cross-sectional view of a bushing holder modified according to one embodiment of the present invention, with a prior art bushing positioned within the bushing holder.

FIGS. 6 to 8 show a modified bushing holder according to the present invention. Bushing holder (200) has inner face (205) and outer face (210), external circumference (215) and internal circumference (220) surrounding bore (225). Bore (225) passes through bushing holder (200) from inner face (205) to outer face (210). Outer face (210) interfaces with the plunger seal (not shown) and the plunger (not shown) passes through bore (225).

Internal circumference (220) has grooves (230) cut into it, passing a short distance (approximately 1 cm in this example) along bore (225) from the inner face (205). These grooves allow passage of steam through bushing holder (200) during the sterilisation protocol, thus enabling steam to reach to the back of the plunger seal.

FIGS. 6 to 8 additionally show a prior art bushing that may be positioned within bore (225) of bushing holder (200). In FIG. 8 the prior art bushing is shown in position within bushing holder (200) so that the outer surface of the bushing is in contact with internal circumference (220) of the bushing holder.

Figure 9:
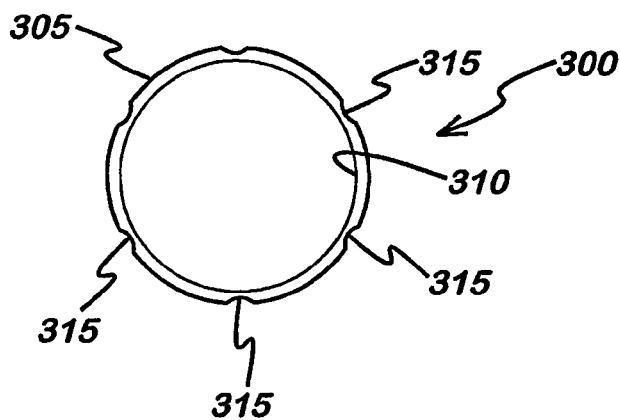
FIGS. 9 and 10 are cross-sectional views of bushings modified according to two embodiments of the present invention.
Figure 10:
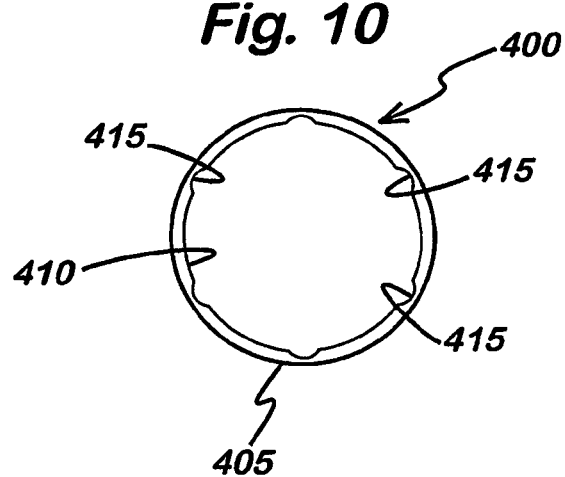

FIGS. 9 and 10 show two examples of bushings modified according to the present invention to enable passage of steam to the back of the seal during the sterilisation process.

In more detail, FIG. 9 shows bushing (300) having outer surface (305) and inner surface (310). Grooves (315) are formed in outer surface (305) to allow passage of steam around the outside of the bushing, between the bushing and the bushing holder.

FIG. 10 shows an alternative bushing of the invention (400) having outer surface (405) and inner surface (410). Grooves (415) are formed in inner surface (410) to allow passage of steam around the inside of the bushing, between the bushing and the plunger barrel.

Figure 11:
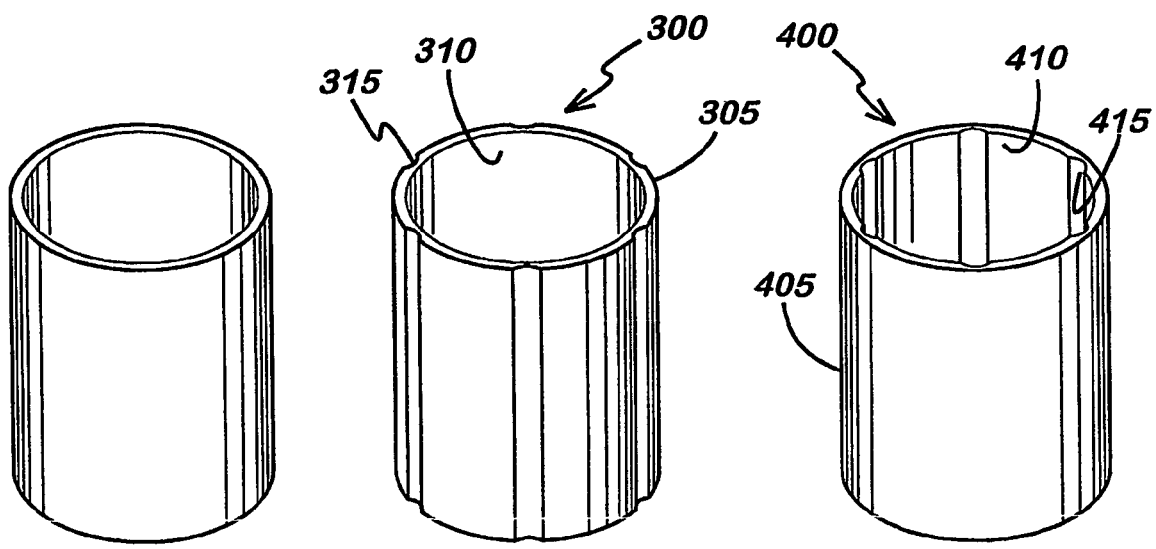
FIG. 11 shows isometric views of a prior art bushing and two bushings modified according to two embodiments of the present invention.
Figure 12:
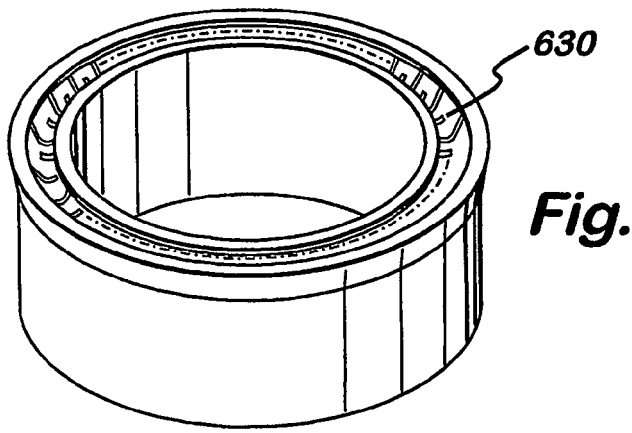
FIG. 12 is an isometric view of a prior art plunger seal.

FIG. 11 shows a prior art bushing (no grooves), and bushings (300) and (400) according to the present invention.

Figure 13:
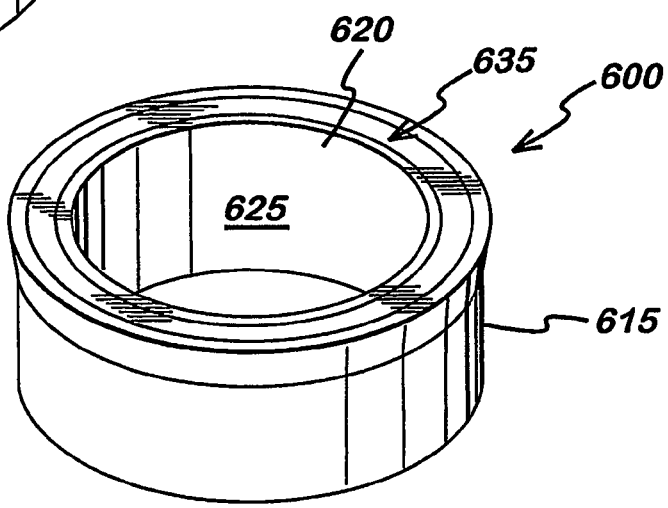
FIGS. 13 and 14 are, respectively, an isometric view and a cross-sectional view of a plunger seal according to one embodiment of the present invention.
Figure 14:
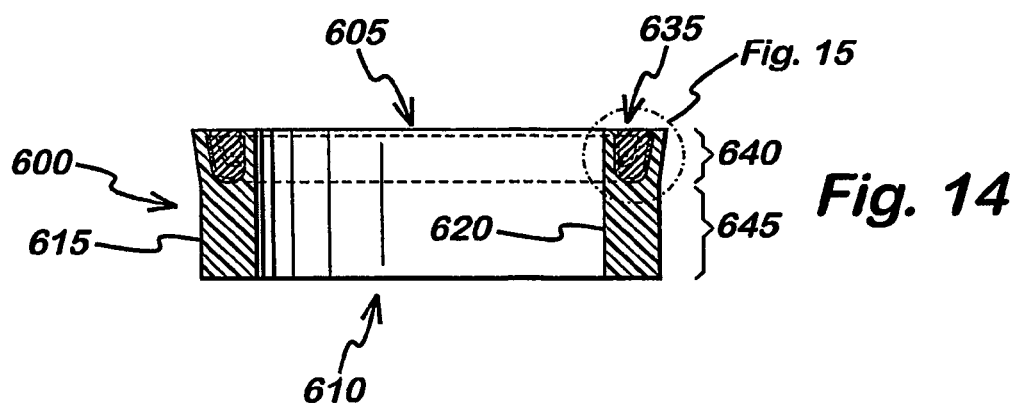
Figure 15:
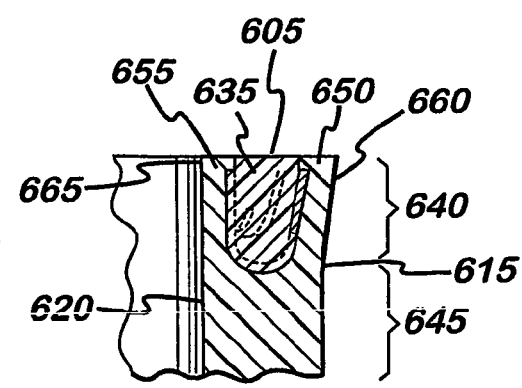
FIG. 15 is a cross-sectional view of a close-up of the region of the seal marked on FIG. 14 by a dotted circle.

FIGS. 12 to 15 show a prior art plunger seal (FIG. 12) and a modified plunger seal (600) (FIGS. 13 to 15). In the prior art seal, the spring retainer (630) is visible within a recess in the upper portion of the seal.

Modified plunger seal (600) is shown in isometric view in FIG. 13, and in cross section in FIG. 14. FIG. 15 shows in cross-section the region outlined by a dotted circle on FIG. 14. Plunger seal (600) has outer face (605), and inner face (610). When the plunger seal is placed into a plunger barrel, outer face (605) is in contact with the suspension in the plunger barrel and inner face (610) faces the outer face of bushing holder (200). Outer face (610) is not visible in FIG. 13. Plunger seal (600) has outer side (615), which is in contact with the plunger barrel, and inner side (620) which surrounds bore (625) through which the plunger passes.

The body of modified plunger seal (600) has an upper portion (640) which meets outer face (605) and a lower portion (645), which meets inner face (610). Upper body portion (640) is in the form of a cup, as can be seen most clearly in FIG. 15. The cup sides (650) and 655) are outwardly deformable and, in use, outer edge (660) and inner edge (665) of the cup sides make sealing contact with, respectively, the plunger barrel and plunger. Between cup sides (650) and (655) is a recess, comprising a brace (635) of resilient plastics material.

The purpose of brace (635) is to prevent cup sides (650) and (655) from collapsing under low pressure, such as when the particle-size reduction apparatus is at rest. Brace (635) is, however, made of sufficiently flexible material to allow cup sides (650) and (655) to deform outwardly during operation of the apparatus.

Plunger seal (600) may have a spring retainer disposed in the cup part of upper body portion (640), however, this is not shown in FIGS. 13-15.

Figure 16:
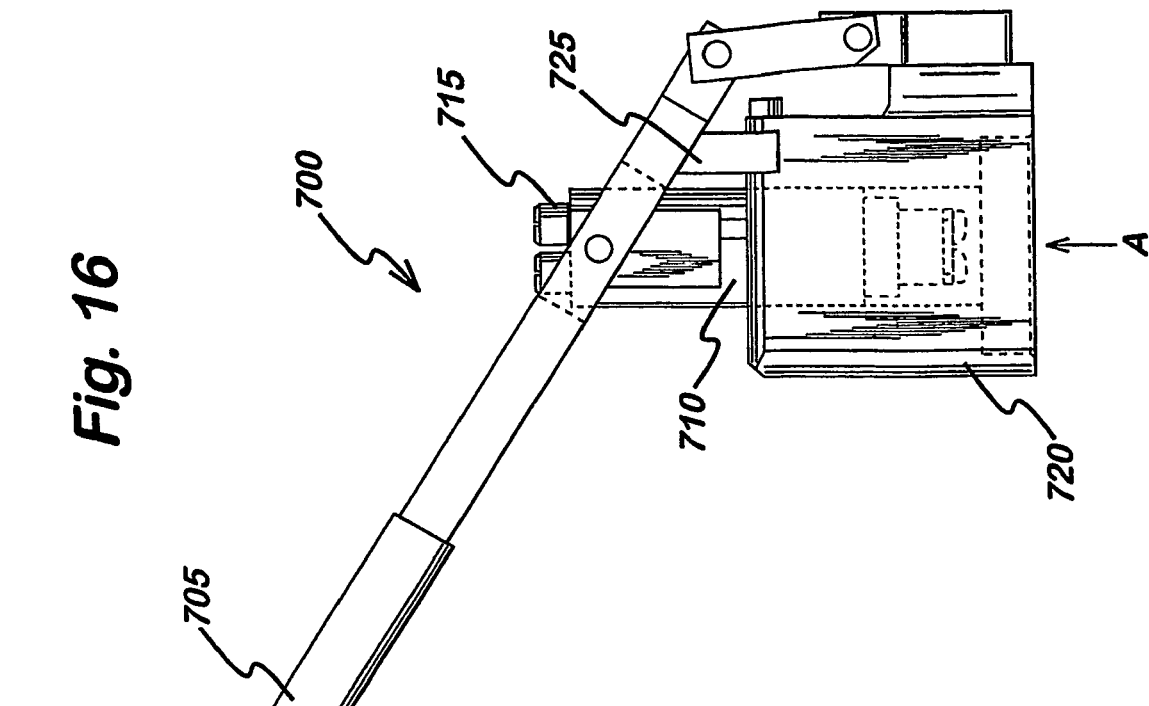
FIGS. 16 and 17 are isometric views of a seal retractor according to one embodiment of the present invention.
Figure 17:
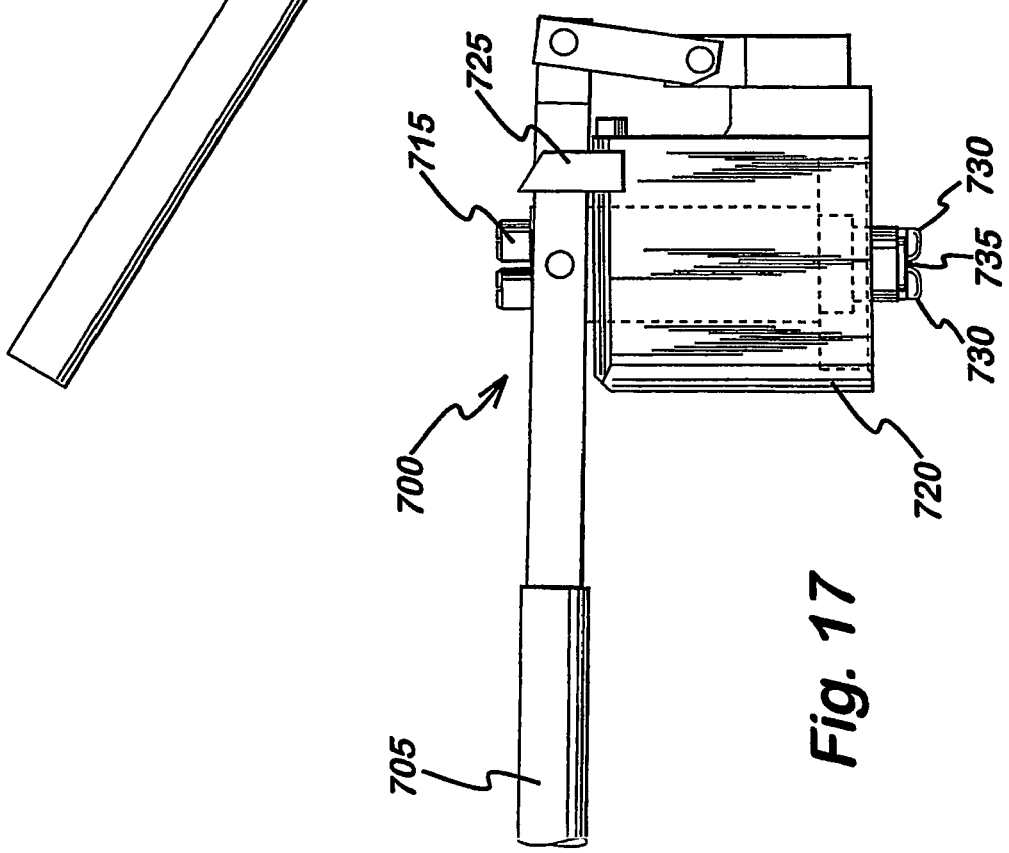

FIGS. 16 and 17 show a seal retractor (700) according to the present invention. FIG. 16 shows the seal retractor in the raised position and FIG. 17 shows the seal retractor in the lowered position. The seal retractor has a handle (705), shaft (710), rotatable knobs (715), attachment means (720) and lock (725). Attachment means (720) has a screw thread to enable attachment of seal retractor (700) to the plunger barrel for insertion or removal of a seal. Lock (725) locks handle (705) and hence shaft (710) in the raised position. Rotatable knobs (715) are connected through shaft (710) to projections (730) at the terminus (735) of shaft (710) and rotation of knobs (715) causes rotation of the projections between projected and retracted positions.

FIGS. 18 to 21 show close-up views of seal retractor (700) viewed along line A marked on FIG. 16.

Figure 18:
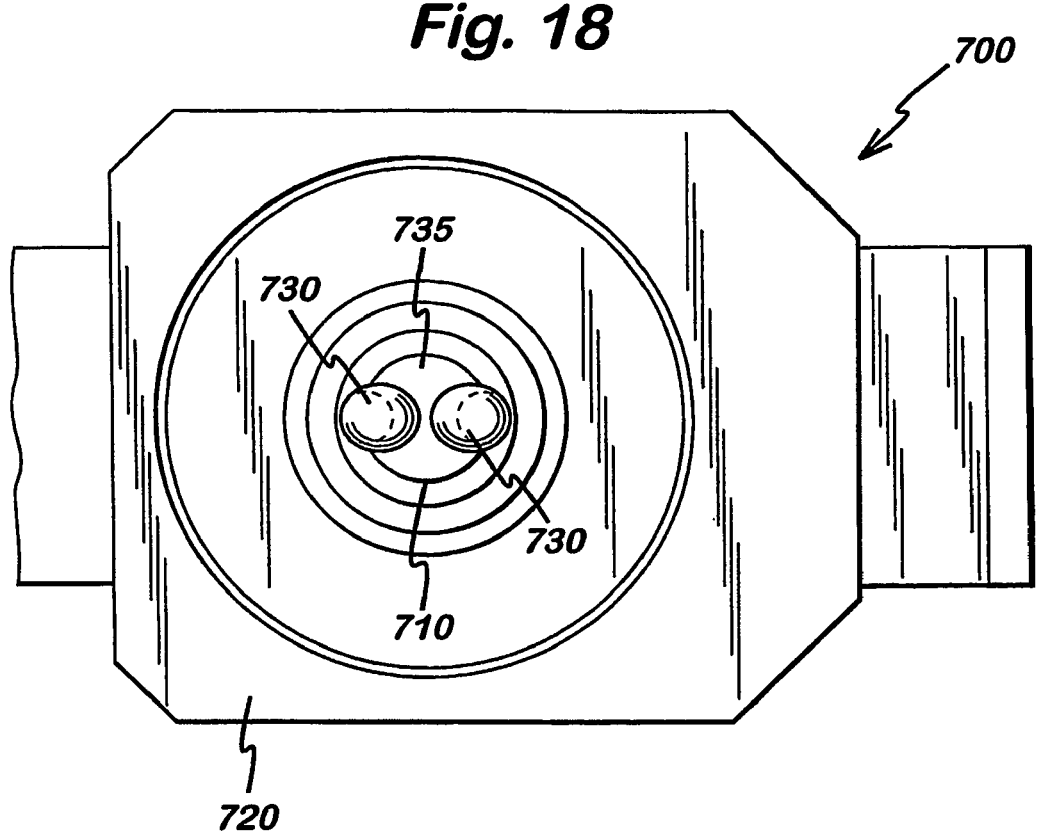
FIGS. 18 to 21 show the terminus of the seal retractor shaft according to one embodiment of the present invention, viewed along the line marked 'A' in FIG. 16.
Figure 19:
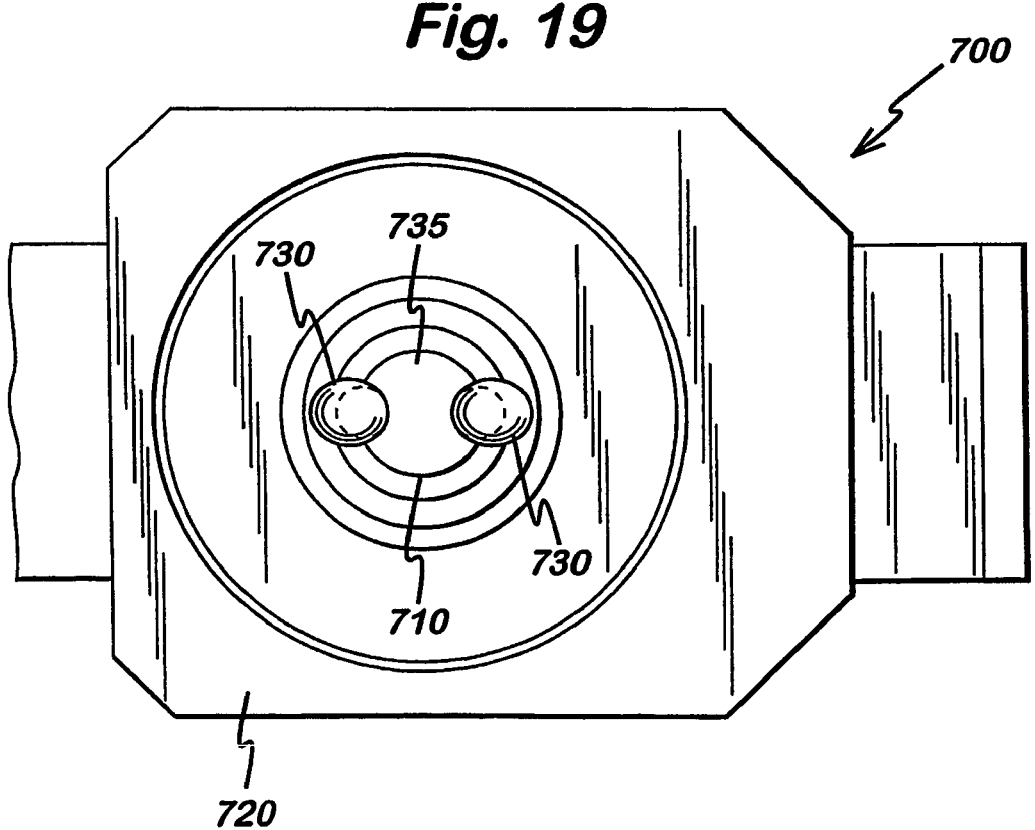

FIGS. 18 and 19 show seal retractor (700) with shaft (710) in the lowered position. Projections (730) are visible at shaft terminus (735). In FIG. 18, projections (730) are in the retracted position. In FIG. 19, projections (730) are in the projected position.

FIGS. 20 and 21 show seal retractor (700) with shaft (710) in the lowered position, with seal (600) fixed onto shaft terminus (735) by projections (730). In FIG. 20, projections (730) are in the retracted position. In FIG. 21, projections (730) are in the projected position and hence seal (600) is secured to shaft terminus (735).

FIG. 22 is a cross-sectional view of the seal retractor. FIG. 22 shows seal retractor (700) with shaft (710) locked in the raised position by lock (725). Seal (600) is fixed onto shaft terminus (735) by projections (730). Seal support rings (740) are positioned behind the seal. Rotatable knobs (715) are connected via connecting rods (745) to projections (730) through shaft (710), and rotation of knobs (715) causes rotation of projections (730) between projected and retracted positions. In FIG. 22, the projections are shown in the retracted position.

FIG. 23 is a part-cross-sectional view of seal retractor (700), in which shaft (710) is in the lowered position, with projections (730) in the retracted position. Seal (600) and seal support rings (740) are shown below seal retractor (700).

EXAMPLES

Example 1

Sterilising a Particle-Size Reduction Apparatus

Protocol

The sterilisation protocol of the invention has been developed for a known particle size reduction apparatus, namely a Microfluidics standard MF-210C Microfluidizer(®), as part of a manufacturing process to provide sterile Budesonide suspensions for Blow-Fill-Seal production of nebulisation suspensions. The protocol is nevertheless believed to be of application to suspensions of other drugs and also to particle-size reduction using other equipment.

As an initial step, we demonstrated the ability to inactivate high levels of contamination of an isolated intensifier and check valves, and the following protocol was then developed for sterilisation of the whole apparatus, to ensure that sterilising temperatures can be achieved throughout the product contact areas and in the isolation chambers of the intensifier.

The protocol is designed to provide the temperatures and exposure times required to achieve a minimum of 121° C. for 15 minutes, using either saturated steam, or superheated water under pressure, or both, and to provide a $10^6$ reduction in *G. stearothermophilus* ATCC 7953 spores when inoculated onto components of the Microfluidizer considered likely to represent the most difficult challenge to sterilisation. The protocol is designed to arrive at a set of operating conditions for sterilisation in place using moist heat, employing either saturated steam or superheated water under pressure or both, which maintains at least 121° C. at internal monitoring sites. The protocol may be modified and developed in future to determine an adjusted minimum sterilising condition, including a minimum sterilising time which in future sterilisation methods may be increased to allow a margin of error in those methods.

This protocol covers the procedures to be followed during the sterilisation process. The apparatus is provided with a number of pressure transducers, and Resistance Temperature Detectors (RTDs) fitted for routine monitoring and during these studies the outputs of the RTDs and pressure transducers are fed to the validator (a Kayo Validator). Additional study thermocouples are positioned internally throughout the apparatus, wherever access is possible. Additional study thermocouples may be positioned externally to help indicate potential sites for routine monitoring.

The equipment and materials used are Microfluidizer(®) Apparatus and Services, a Kaye Validator 2000, a Kaye Calibration Temperature source HTR400 or LTR140 or CTR40, or alternative equivalent provided by the applicant and a Kaye IRTD calibration reference thermometer.

All critical operating instruments used in the sterilising procedures covered by this protocol are calibrated, using standards traceable to national standards. All critical test instruments used in the protocol are calibrated according to written procedures, using standards traceable to national standards.

During the sterilisation process covered by this protocol, observations of routine temperature and pressure indicators are made, and may be modified prior to or during the studies to reflect the number of study temperature and pressure test positions built into the apparatus for these studies. Validation thermocouple data are automatically logged at a minimum frequency of every ten seconds from when heat is introduced into the test apparatus.

Test temperature sensors and the data recorder are calibrated at 100° C. and 130° C., after the test thermocouples have stabilized to under 0.2° C. per minute for 5 minutes, with the reference thermometer stabilized to within 0.012° C. during the final minute. Readings of each sensor and reference thermometer are taken at one minute intervals for five minutes at each temperature point. Calibration of test sensors and data recorder are confirmed at 122° C. before and after qualification.

Temperatures derived from sensors and data recorder should not vary from reference temperatures by more than ±0.5° C. Only thermocouples meeting these criteria are used in the qualification.

A series of studies is conducted employing saturated steam or superheated water under pressure, to provide sterilising conditions throughout the product circuit and in the isolation chambers. The pipework is adjusted to provide suitable services for the heat source employed.

The studies are conducted over a range of temperatures and times (and, if necessary, pressures for the superheated water), until a suitable set of conditions is achieved which complies with the acceptance criteria. At least three consecutive acceptable studies are performed with unchanged sterilising settings before those settings can be considered the minimum suitable for further validation study.

Up to nine of the routine RTD temperature sensors supplied with the equipment and additional study thermocouples to a total of 36 sensors, including pressure transducers, are positioned in and on the apparatus. Internal thermocouples are introduced via appropriate Triclover(®) seals. External thermocouples may if desired be held in direct contact with the stainless steel surfaces.

Data collection commences when heat is applied to the product contact circuit, and the isolation chamber, data being collected simultaneously from each temperature sensor, and each pressure sensor.

The time at which the first temperature probe reaches a minimum of 121° C., and at which all temperature probes reach 121° C. is recorded. The timed holding period commences when all test thermocouples have reached 121° C., and continues until all test thermocouples have remained above 121° C. continuously for a minimum of 15 minutes. At the end of the holding period, the apparatus is cooled. For steam sterilisations, the equipment is pressurised with air, and the steam pressure terminated. For superheated water sterilisations, the water in the circuit is cooled.

Results obtained from the above analyses must show compliance with the following criteria for any set of sterilising conditions to be considered to provide minimum conditions for further study:

1—All internal temperature test positions must record a minimum of 121° C. continuously for at least the final 15 minutes of the holding period.

2—For steam sterilisation, pressures measured must agree with the saturated vapour pressure of steam at the temperature measured at the same point, within plus or minus 1° C.

Results 18 steam sterilisation protocols were carried out according to the protocol described above. The first run was a control (no spores) and in the remaining 17 runs the following components of an M-210EH Microfluidizer(®) were inoculated with $2 \times 10^6$ heat resistant spores of *Geobacillus stearothermophilus* ATCC No. 7953:

Runs 2-4 check valve spring retainer, intensifier plunger seal, plunger contact sealing edge.

Runs 5-7 intensifier plunger seal, outer wall, behind barrel contact sealing edge.

Runs 8-10 intensifier plunger seal, spring contact surface.

Runs 11-13 plunger bushing inner surface

Runs 14-16 plunger bushing outer surface, plastic seal support ring, surface in contact with metal seal support ring.

Run 17 plunger bushing outer surface, plastic seal support ring, surface in contact with metal seal support ring, PTFE sealed-spring plunger seal.

Run 18 plunger bushing inner surface, plastic seal support ring, surface in contact with metal seal support ring, Ultra High Density PE sealed-spring plunger seal.

The steam sterilisation protocols were run to achieve 121° C. for 15 minutes (as measured using a temperature probe embedded in one intensifier barrel, close to the position of the plunger seal).

After this time, each inoculated component was then tested for sterility according to Example 4 below. All components showed a 6 log reduction in heat-resistant spores—i.e. all components passed the sterility test (MCA guidelines).

Example 2

Inserting a Seal

The seal components (seal and seal support rings) were placed onto the seal retractor and secured to the shaft terminus by turning the cams outwards. The pump barrel was removed from the apparatus and placed in a vice, and the seal retractor was screwed onto the barrel. The seal retractor handle was lowered, thus lowering the seal into the barrel to the correct position. The cams were then turned inwards to release the seal from the seal retractor. The handle was then lifted to raise the seal retractor shaft from the barrel, leaving the seal in situ, and the seal retractor was unscrewed from the barrel.

Example 3

Removing a Seal

The pump barrel was placed in a vice, and the seal retractor was screwed to the barrel. The cams were turned inwards to the retracted position and the handle was pushed down to lower the seal retractor shaft into the barrel and through the seal. Then, the cams were turned outwards to contact the lips of the seal, thus securing the seal to the seal retractor shaft. The handle was then raised, thus lifting the seal out of the barrel on the end of the seal retractor shaft. The device was unscrewed from the barrel, and the cams were turned inwards to enable the seal components to be removed.

Example 4

Validating Sterility of a Seal

A seal, which has previously been contaminated with at least $1 \times 10^6$ heat-resistant bacterial spores, is inserted into the bore of a particle-size reduction apparatus as described in Example 2 above. The particle-size reduction apparatus is sterilised as described in Example 1 above and then the seal is removed from the apparatus as described in Example 3 above. To validate the sterility of the apparatus bore, the seal is incubated with growth medium. A seal removed from an apparatus that has not undergone a sterilisation procedure is used as a control. The growth medium is examined for growth of microorganisms, which would indicate that the test seal (and hence the bore) had not been sterilised effectively. If there is no growth in the medium comprising the test seal, (growth being observed in the medium comprising the seal from the unsterilised bore) this indicates that sterility is achieved.

Example 5

Reduction of Particle Size of a Sterile Suspension

The mass median diameter of particles of a Budesonide suspension is reduced using an M-210EH Microfluidizer(®) apparatus that has previously been sterilised according to Example 1 above.

A sterile Budesonide suspension (12 liters) having particles of mass median diameter approximately 50 μm is introduced into the sterile apparatus from the reaction feed tank. The pressure used is approximately 20,000 psi and the apparatus is run at 1.2 liters per minute. The suspension is passed through the apparatus and particle size is monitored during each pass. After about 14 passes (approximately 2 hours 20 minutes) the mass median diameter of particles in the suspension is reduced to 2-3 μm. The suspension is then transferred to a sterile packaging line for packaging into sterile nebules.

The invention claimed is:

1. A method of producing a comminuted sterile suspension of particles, which comprises:

subjecting an initial sterile suspension of particles to a comminution procedure carried out in a sterilized particle size reduction apparatus, said particle size reduction apparatus comprising an interaction chamber for reducing the particle size of the suspension, an intensifier for introducing the suspension into the interaction chamber at high pressure, and a conduit between the interaction chamber and the intensifier, said conduit comprising a sterilizable diaphragm needle valve, wherein the intensifier comprises a reciprocating plunger and a bushing assembly to guide the plunger, said bushing assembly comprising a channel in or on the surface of the bushing assembly; and recovering a suspension of particles of reduced size;

wherein the method comprises sterilization wherein at least surfaces of the apparatus contacting the suspension are sterilized, wherein said sterilization comprises passing steam or water through the bushing assembly while the plunger is in place.

2. A method according to claim 1, wherein the sterile suspension comprises Budesonide or Fluticasone.

3. A method according to claim 1, comprising monitoring particle size until a final particle size in the suspension of mass median diameter 2 μm-3 μm is obtained.

4. A method according to claim 1, further comprising packaging the sterile suspension into sterile ampoules.

5. The method of claim 1, wherein the intensifier comprises a plunger rod connected via a threaded cam nut to a connecting rod, at one end of which connecting rod is a screw thread to receive the cam nut, and wherein the dimensions of the screw thread and the thread of the cam nut are such that as the nut is screwed onto the connecting rod respective mating services of the cam nut and the connecting rod mate simultaneously.

6. The method of claim 1, wherein the sterilizable diaphragm needle valve has a metal-to-metal seat.

7. The method of claim 1, wherein the intensifier comprises an output and an input, and the interaction chamber comprises an input and an output, the output of the intensifier being connected to the input of the interaction chamber and the output of the interaction chamber being connected to the input of the intensifier, and wherein there is no conduit between the output of the intensifier and the input of the intensifier other than via the interaction chamber.

8. The method of claim 1, wherein the seal is an annular high-pressure seal for a plunger reciprocating within a barrel, comprising upper and lower body portions being in the form of a cup and having sides surrounding a recess, the sides being outwardly deformable so that respective outer and inner edges of the sides of the cup make, in use, sealing contact with respectively the barrel and the plunger, the seal further comprising a brace to prevent the sides from collapsing into the recess under low pressure and wherein the brace comprises a resilient plastic material.

9. The method of claim 8, wherein said brace presents a smooth surface free from cavities.

10. The method of claim 8, wherein said seal comprises virgin PTFE or glass-strengthened PTFE.

11. A method of producing a comminuted sterile suspension of particles, comprising subjecting an initial sterile suspension of particles to a comminution procedure carried out in a sterilized particle size reduction apparatus, said particle size reduction apparatus comprising (i) an interaction chamber for reducing the particle size of the suspension, (ii) an intensifier for introducing the suspension into the interaction chamber at high pressure, (iii) a sterilizable diaphragm needle valve in a conduit between the intensifier and the interaction chamber, (iv) a reciprocating plunger, and (v) a bushing assembly to guide the plunger comprising a channel in or on the surface of the bushing assembly to allow steam or water to pass through the bushing assembly while the plunger is in place;

sterilizing the particle size reduction apparatus by passing steam or water through the sterilizable diaphragm needle valve and passing steam or water through the bushing assembly while the plunger is in place; and recovering a suspension of particles of reduced size.

* * * * *

UNITED STATES PATENT AND TRADEMARK OFFICE
CERTIFICATE OF CORRECTION

PATENT NO.        : 7,600,703 B2
APPLICATION NO. : 10/568726
DATED             : October 13, 2009
INVENTOR(S)       : Greenwood et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 340 days.

Signed and Sealed this

Fifth Day of October, 2010

David J. Kappos
*Director of the United States Patent and Trademark Office*